United States Patent [19]

Lin et al.

[11] Patent Number: 5,852,173
[45] Date of Patent: Dec. 22, 1998

[54] TNF RECEPTOR DEATH LIGAND PROTEINS AND INHIBITORS OF LIGAND BINDING

[75] Inventors: Lih-Ling Lin, Concord; Jennifer Chen, Chestnut Hill; Andrea R. Schievella, Winchester; James Graham, Somerville, all of Mass.

[73] Assignee: Genetics Institute, Inc., Cambridge, Mass.

[21] Appl. No.: 533,901

[22] Filed: Sep. 26, 1995

Related U.S. Application Data

[63] Continuation-in-part of Ser. No. 494,440, Jun. 19, 1995, which is a continuation-in-part of Ser. No. 327,514, Oct. 19, 1994, abandoned.

[51] Int. Cl.$^6$ .......................... C07K 17/47; C07K 14/52; C12N 15/10
[52] U.S. Cl. ................................ 530/350; 514/2; 514/12; 435/69.1; 435/325; 530/300; 530/351
[58] Field of Search ..................................... 435/69.1, 325, 435/252.3, 254.11; 514/2, 12; 424/139.1, 143.1; 530/350, 351, 388.22, 388.23

[56] References Cited

U.S. PATENT DOCUMENTS

| | | | |
|---|---|---|---|
| 5,296,592 | 3/1994 | Dower et al. | 530/413 |
| 5,464,938 | 11/1995 | Smith et al. | 530/350 |
| 5,506,340 | 4/1996 | Heavner | 530/324 |
| 5,563,039 | 10/1996 | Goeddel et al. | 435/7.1 |

FOREIGN PATENT DOCUMENTS

| | | |
|---|---|---|
| 46127/93 | 9/1993 | Australia . |
| 308378 | 3/1989 | European Pat. Off. . |
| 433900 | 6/1991 | European Pat. Off. . |
| 526905 | 2/1993 | European Pat. Off. . |
| 0 585 939 A2 | 9/1993 | European Pat. Off. . |
| WO 92/03470 | 3/1992 | WIPO . |
| WO 92/03471 | 3/1992 | WIPO . |
| WO 92/14834 | 9/1992 | WIPO . |
| WO 93/19777 | 10/1993 | WIPO . |
| WO 94/01548 | 1/1994 | WIPO . |
| WO 94/10207 | 5/1994 | WIPO . |
| WO 95/31544 | 11/1995 | WIPO . |
| WO 95/33051 | 12/1995 | WIPO . |
| WO 96/25941 | 8/1996 | WIPO . |

OTHER PUBLICATIONS

Stites et al., Eds, Basic and Clinical Immunology, Appleton & Lange: Norwalk, CT, pp. 137–150, 1994.
Darnell et al., Molecular Cell Biology, Scientific American Books: USA, pp. 160–163, 1986.
Luban and Goff, 1995, Curr. Opin. Biotech. 6: 59–64.
GenBank–Accession No. U44953; 01 Jul. 1996.
GenBank Accession No. U48254; 03 Aug. 1996.
Miki et al. (1992) Cancer Res. 52:643.
Darnay et al. (1994) J. Biol. Chem. 269: 20299.
Kiefer et al. (1992) J. Biol. Chem. 267: 12692.
Genbank accession number T08593 (1993).
Genbank accession number TO7800 (1993).
Genbank accession number M78050 (1992).
Genbank accession number M78539 (1992).
Tartaglia et al., Tumor necrosis factor receptor signaling, J. Biol. Chem., 267(7): 4304–4307, Mar. 1992.
Tartaglia et al., Tumor necrosis factor's cytotoxic activity is signaled by the p55 TNF receptor, Cell, 73: 213–216, Apr. 1993.
Schall et al., Cell 61:361–370 (1990).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Gyuris et al., Cell 75:791–803 (1993).
Gietz et al., Nucleic Acids Res. 20:1425 (1992).
Waye et al., Protein Engineering 8:90 (1995).
Auffray et al., Life Sciences 318:263–272 (1995).
Rothe et al., Cell 78:681–692 (1994).
Song et al., The Journal of Biological Chemistry 269:22492–22495 (1994).
Tartaglia et al., Cell 74:845–853 (1993).
Boldin et al., The Journal of Biological Chemistry 270(1):387–391 (1995).
Hsu et al., Cell 81:495–504 (1995).
Boldin et al., FEBS Letters 367:39–44 (1995).

*Primary Examiner*—Stephen Walsh
*Assistant Examiner*—Claire M. Kaufman
*Attorney, Agent, or Firm*—Suzanne A. Sprunger; Scott A. Brown; Thomas J. DesRosier

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

7 Claims, 8 Drawing Sheets

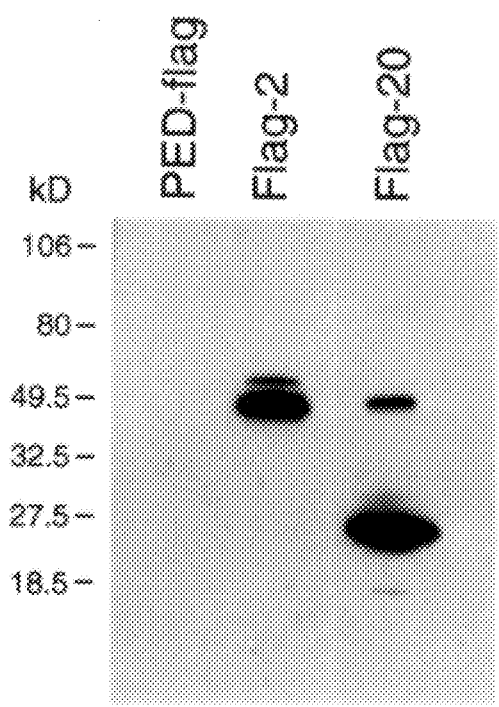

Fig. 4
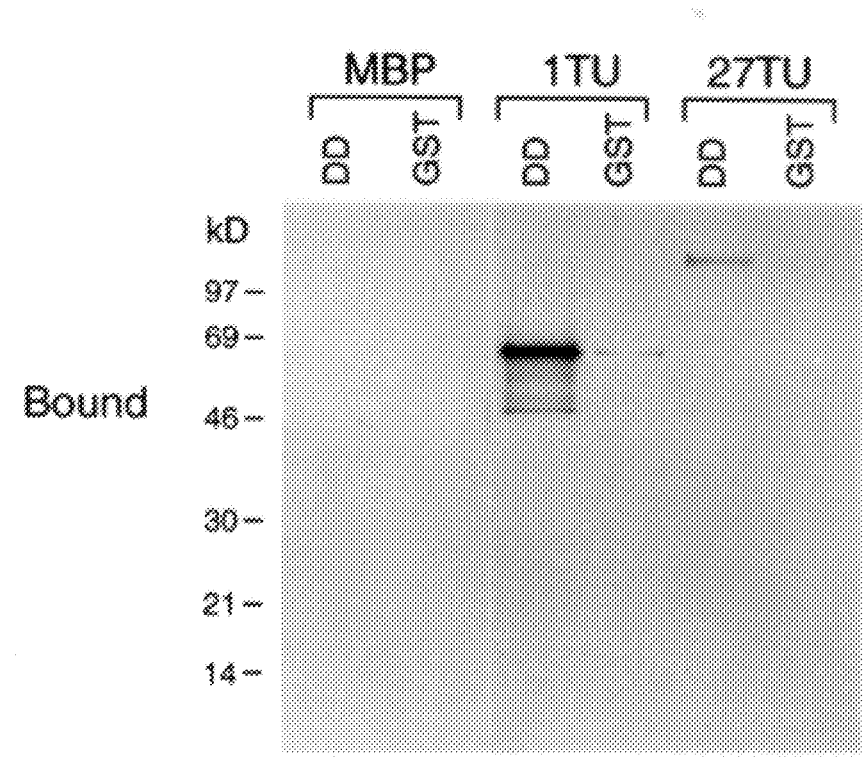
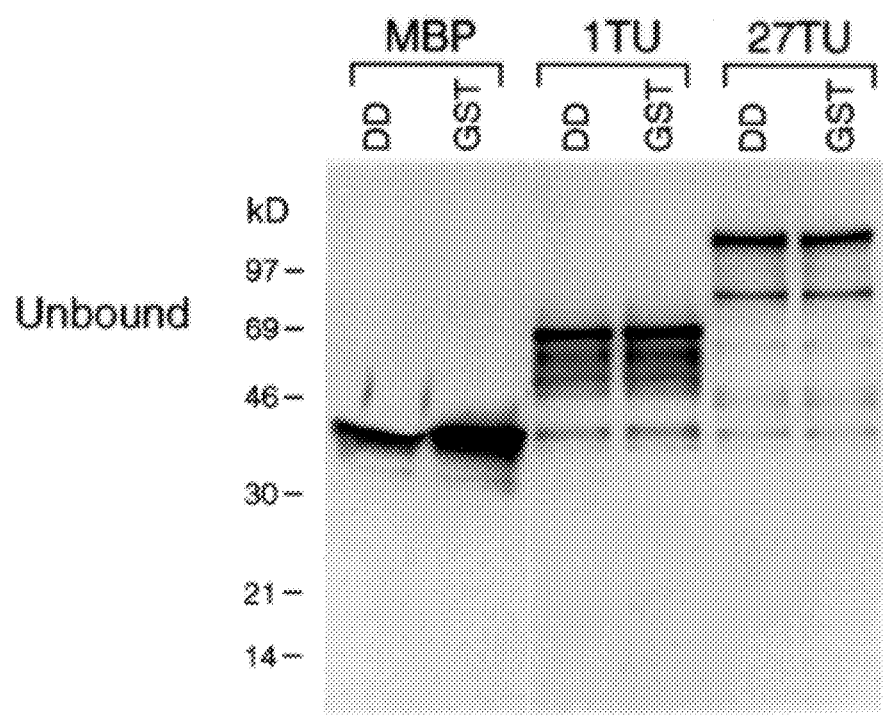

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2158 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i x ) FEATURE:
( A ) NAME/KEY: CDS
( B ) LOCATION: 2..1231

( x i ) SEQUENCE DESCRIPTION: SEQ ID NO:1:

```
C  AGC  AAT  GCA  GGT  GAT  GGA  CCA  GGT  GGC  GAG  GGC  AGT  GTT  CAC  CTG              46
   Ser  Asn  Ala  Gly  Asp  Gly  Pro  Gly  Gly  Glu  Gly  Ser  Val  His  Leu
   1                  5                       10                      15

GCA  AGC  TCT  CGG  GGC  ACT  TTG  TCT  GAT  AGT  GAA  ATT  GAG  ACC  AAC  TCT              94
Ala  Ser  Ser  Arg  Gly  Thr  Leu  Ser  Asp  Ser  Glu  Ile  Glu  Thr  Asn  Ser
                    20                       25                      30

GCC  ACA  AGC  ACC  ATC  TTT  GGT  AAA  GCC  CAC  AGC  TTG  AAG  CCA  AGC  ATA             142
Ala  Thr  Ser  Thr  Ile  Phe  Gly  Lys  Ala  His  Ser  Leu  Lys  Pro  Ser  Ile
                    35                       40                      45

AAG  GAG  AAG  CTG  GCA  GGC  AGC  CCC  ATT  CGT  ACT  TCT  GAA  GAT  GTG  AGC             190
Lys  Glu  Lys  Leu  Ala  Gly  Ser  Pro  Ile  Arg  Thr  Ser  Glu  Asp  Val  Ser
          50                       55                      60

CAG  CGA  GTC  TAT  CTC  TAT  GAG  GGA  CTC  CTA  GGC  AAA  GAG  CGT  TCT  ACT             238
Gln  Arg  Val  Tyr  Leu  Tyr  Glu  Gly  Leu  Leu  Gly  Lys  Glu  Arg  Ser  Thr
          65                       70                      75

TTA  TGG  GAC  CAA  ATG  CAA  TTC  TGG  GAA  GAT  GCC  TTC  TTA  GAT  GCT  GTG             286
Leu  Trp  Asp  Gln  Met  Gln  Phe  Trp  Glu  Asp  Ala  Phe  Leu  Asp  Ala  Val
80                       85                      90                      95

ATG  TTG  GAG  AGA  GAA  GGG  ATG  GGT  ATG  GAC  CAG  GGT  CCC  CAG  GAA  ATG             334
Met  Leu  Glu  Arg  Glu  Gly  Met  Gly  Met  Asp  Gln  Gly  Pro  Gln  Glu  Met
                    100                      105                     110

ATC  GAC  AGG  TAC  CTG  TCC  CTT  GGA  GAA  CAT  GAC  CGG  AAG  CGC  CTG  GAA             382
Ile  Asp  Arg  Tyr  Leu  Ser  Leu  Gly  Glu  His  Asp  Arg  Lys  Arg  Leu  Glu
                    115                      120                     125

GAT  GAT  GAA  GAT  CGC  TTG  CTG  GCC  ACA  CTT  CTG  CAC  AAC  CTC  ATC  TCC             430
Asp  Asp  Glu  Asp  Arg  Leu  Leu  Ala  Thr  Leu  Leu  His  Asn  Leu  Ile  Ser
          130                      135                     140

TAC  ATG  CTG  CTG  ATG  AAG  GTA  AAT  AAG  AAT  GAC  ATC  CGC  AAG  AAG  GTG             478
Tyr  Met  Leu  Leu  Met  Lys  Val  Asn  Lys  Asn  Asp  Ile  Arg  Lys  Lys  Val
     145                      150                     155

AGG  CGC  CTA  ATG  GGA  AAG  TCG  CAC  ATT  GGG  CTT  GTG  TAC  AGC  CAG  CAA             526
Arg  Arg  Leu  Met  Gly  Lys  Ser  His  Ile  Gly  Leu  Val  Tyr  Ser  Gln  Gln
160                      165                      170                     175

ATC  AAT  GAG  GTG  CTT  GAT  CAG  CTG  GCG  AAC  CTG  AAT  GGA  CGC  GAT  CTC             574
```

|     |     |     |     |     |     |     |     |     |     |     |     |     |     |      |
| --- | --- | --- | --- | --- | --- | --- | --- | --- | --- | --- | --- | --- | --- | ---- |
| Ile | Asn | Glu | Val | Leu | Asp | Gln | Leu | Ala | Asn | Leu | Asn | Gly | Arg | Asp Leu |
|     |     |     |     | 180 |     |     |     | 185 |     |     |     |     | 190 |      |

```
TCT ATC TGG TCC AGT GGC AGC CGG CAC ATG AAG AAG CAG ACA TTT GTG        622
Ser Ile Trp Ser Ser Gly Ser Arg His Met Lys Lys Gln Thr Phe Val
        195             200                 205

GTA CAT GCA GGG ACA GAT ACA AAC GGA GAT ATC TTT TTC ATG GAG GTG        670
Val His Ala Gly Thr Asp Thr Asn Gly Asp Ile Phe Phe Met Glu Val
            210             215                 220

TGC GAT GAC TGT GTG GTG TTG CGT AGT AAC ATC GGA ACA GTG TAT GAG        718
Cys Asp Asp Cys Val Val Leu Arg Ser Asn Ile Gly Thr Val Tyr Glu
    225             230                 235

CGC TGG TGG TAC GAG AAG CTC ATC AAC ATG ACC TAC TGT CCC AAG ACG        766
Arg Trp Trp Tyr Glu Lys Leu Ile Asn Met Thr Tyr Cys Pro Lys Thr
240             245                 250                 255

AAG GTG TTG TGC TTG TGG CGT AGA AAT GGC TCT GAG ACC CAG CTC AAC        814
Lys Val Leu Cys Leu Trp Arg Arg Asn Gly Ser Glu Thr Gln Leu Asn
                260                 265                 270

AAG TTC TAT ACT AAA AAG TGT CGG GAG CTG TAC TAC TGT GTG AAG GAC        862
Lys Phe Tyr Thr Lys Lys Cys Arg Glu Leu Tyr Tyr Cys Val Lys Asp
                275             280                 285

AGC ATG GAG CGC GCT GCC GCC CGA CAG CAA AGC ATC AAA CCC GGA CCT        910
Ser Met Glu Arg Ala Ala Ala Arg Gln Gln Ser Ile Lys Pro Gly Pro
        290             295                 300

GAA TTG GGT GGC GAG TTC CCT GTG CAG GAC CTG AAG ACT GGT GAG GGT        958
Glu Leu Gly Gly Glu Phe Pro Val Gln Asp Leu Lys Thr Gly Glu Gly
305             310                 315

GGC CTG CTG CAG GTG ACC CTG GAA GGG ATC AAC CTC AAA TTC ATG CAC       1006
Gly Leu Leu Gln Val Thr Leu Glu Gly Ile Asn Leu Lys Phe Met His
320             325                 330                 335

AAT CAG GTT TTC ATA GAG CTG AAT CAC ATT AAA AAG TGC AAT ACA GTT       1054
Asn Gln Val Phe Ile Glu Leu Asn His Ile Lys Lys Cys Asn Thr Val
                340                 345                 350

CGA GGC GTC TTT GTC CTG GAG GAA TTT GTT CCT GAA ATT AAA GAA GTG       1102
Arg Gly Val Phe Val Leu Glu Glu Phe Val Pro Glu Ile Lys Glu Val
                355                 360                 365

GTG AGC CAC AAG TAC AAG ACA CCA ATG GCC CAC GAA ATC TGC TAC TCC       1150
Val Ser His Lys Tyr Lys Thr Pro Met Ala His Glu Ile Cys Tyr Ser
        370                 375                 380

GTA TTA TGT CTC TTC TCG TAC GTG GCT GCA GTT CAT AGC AGT GAG GAA       1198
Val Leu Cys Leu Phe Ser Tyr Val Ala Ala Val His Ser Ser Glu Glu
    385             390                 395

GAT CTC AGA ACC CCG CCC CGG CCT GTC TCT AGC TGATGGAGAG GGGCTACGCA     1251
Asp Leu Arg Thr Pro Pro Arg Pro Val Ser Ser
400             405                 410

GCTGCCCCAG CCCAGGGCAC GCCCCTGGCC CCTTGCTGTT CCCAAGTGCA CGATGCTGCT     1311

GTGACTGAGG AGTGGATGAT GCTCGTGTGT CCTCTGCAAG CCCCCTGCTG TGGCTTGGGT     1371

GGGTACCGGT TATGTGTCCC TCTGAGTGTG TCTTGAGCGT GTCCACCTTC TCCCTCTCCA     1431

CTCCCAGAAG ACCAAACTGC CTTCCCCTCA GGGCTCAAGA ATGTGTACAG TCTGTGGGGC     1491

CGGTGTGAAC CCACTATTTT GTGTCCTTGA GACATTTGTG TTGTGGTTCC TTGTCCTTGT     1551

CCCTGGCGTT AACTGTCCAC TGCAAGAGTC TGGCTCTCCC TTCTCTGTGA CCCGGCATGA     1611

CTGGGCGCCT GGAGCAGTTT CACTCTGTGA GGAGTGAGGG AACCCTGGGG CTCACCCTCT     1671

CAGAGGAAGG GCACAGAGAG GAAGGGAAGA ATTGGGGGGC AGCCGGAGTG AGTGGCAGCC     1731

TCCCTGCTTC CTTCTGCATT CCCAAGCCGG CAGCTACTGC CCAGGGCCCG CAGTGTTGGC     1791

TGCTGCCTGC CACAGCCTCT GTGACTGCAG TGGAGCGGCG AATTCCCTGT GGCCTGCCAC     1851

GCCTTCGGCA TCAGAGGATG GAGTGGTCGA GGCTAGTGGA GTCCCAGGGA CCGCTGGCTG     1911
```

```
CTCTGCCTGA GCATCAGGGA GGGGGCAGGA AAGACCAAGC TGGGTTTGCA CATCTGTCTG      1971

CAGGCTGTCT CTCCAGGCAC GGGGTGTCAG GAGGGAGAGA CAGCCTGGGT ATGGGCAAGA      2031

AATGACTGTA AATATTTCAG CCCCACATTA TTTATAGAAA ATGTACAGTT GTGTGAATGT      2091

GAAATAAATG TCCTCACCTC CCAAAAAAAA AAAAAAAAAA AAAAAAAAAA AAAAAAAAA       2151

AAAAAAA                                                                2158
```

( 2 ) INFORMATION FOR SEQ ID NO:2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser Asn Ala Gly Asp Gly Pro Gly Gly Glu Gly Ser Val His Leu Ala
 1               5                  10                  15

Ser Ser Arg Gly Thr Leu Ser Asp Ser Glu Ile Glu Thr Asn Ser Ala
            20                  25                  30

Thr Ser Thr Ile Phe Gly Lys Ala His Ser Leu Lys Pro Ser Ile Lys
        35                  40                  45

Glu Lys Leu Ala Gly Ser Pro Ile Arg Thr Ser Glu Asp Val Ser Gln
    50                  55                  60

Arg Val Tyr Leu Tyr Glu Gly Leu Leu Gly Lys Glu Arg Ser Thr Leu
65                  70                  75                  80

Trp Asp Gln Met Gln Phe Trp Glu Asp Ala Phe Leu Asp Ala Val Met
                85                  90                  95

Leu Glu Arg Glu Gly Met Gly Met Asp Gln Gly Pro Gln Glu Met Ile
               100                 105                 110

Asp Arg Tyr Leu Ser Leu Gly Glu His Asp Arg Lys Arg Leu Glu Asp
           115                 120                 125

Asp Glu Asp Arg Leu Leu Ala Thr Leu Leu His Asn Leu Ile Ser Tyr
       130                 135                 140

Met Leu Leu Met Lys Val Asn Lys Asn Asp Ile Arg Lys Lys Val Arg
145                 150                 155                 160

Arg Leu Met Gly Lys Ser His Ile Gly Leu Val Tyr Ser Gln Gln Ile
                165                 170                 175

Asn Glu Val Leu Asp Gln Leu Ala Leu Asn Gly Arg Asp Leu Ser
               180                 185                 190

Ile Trp Ser Ser Gly Ser Arg His Met Lys Lys Gln Thr Phe Val Val
           195                 200                 205

His Ala Gly Thr Asp Thr Asn Gly Asp Ile Phe Phe Met Glu Val Cys
       210                 215                 220

Asp Asp Cys Val Val Leu Arg Ser Asn Ile Gly Thr Val Tyr Glu Arg
225                 230                 235                 240

Trp Trp Tyr Glu Lys Leu Ile Asn Met Thr Tyr Cys Pro Lys Thr Lys
                245                 250                 255

Val Leu Cys Leu Trp Arg Arg Asn Gly Ser Glu Thr Gln Leu Asn Lys
               260                 265                 270

Phe Tyr Thr Lys Lys Cys Arg Glu Leu Tyr Tyr Cys Val Lys Asp Ser
           275                 280                 285

Met Glu Arg Ala Ala Ala Gln Gln Ser Ile Lys Pro Gly Pro Glu
       290                 295                 300
```

| | | | | | | | | | | | | | | | |
|---|---|---|---|---|---|---|---|---|---|---|---|---|---|---|---|
| Leu | Gly | Gly | Glu | Phe | Pro | Val | Gln | Asp | Leu | Lys | Thr | Gly | Glu | Gly | Gly |
| 305 | | | | | 310 | | | | 315 | | | | | | 320 |
| Leu | Leu | Gln | Val | Thr | Leu | Glu | Gly | Ile | Asn | Leu | Lys | Phe | Met | His | Asn |
| | | | | 325 | | | | 330 | | | | | | 335 | |
| Gln | Val | Phe | Ile | Glu | Leu | Asn | His | Ile | Lys | Lys | Cys | Asn | Thr | Val | Arg |
| | | | 340 | | | | | 345 | | | | | 350 | | |
| Gly | Val | Phe | Val | Leu | Glu | Glu | Phe | Val | Pro | Glu | Ile | Lys | Glu | Val | Val |
| | | | 355 | | | | 360 | | | | | 365 | | | |
| Ser | His | Lys | Tyr | Lys | Thr | Pro | Met | Ala | His | Glu | Ile | Cys | Tyr | Ser | Val |
| | 370 | | | | | 375 | | | | 380 | | | | | |
| Leu | Cys | Leu | Phe | Ser | Tyr | Val | Ala | Ala | Val | His | Ser | Ser | Glu | Glu | Asp |
| 385 | | | | | 390 | | | | | 395 | | | | | 400 |
| Leu | Arg | Thr | Pro | Pro | Arg | Pro | Val | Ser | Ser | | | | | | |
| | | | | 405 | | | | | 410 | | | | | | |

( 2 ) INFORMATION FOR SEQ ID NO:3:

( i ) SEQUENCE CHARACTERISTICS:
        ( A ) LENGTH: 826 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..415

( x i ) SEQUENCE DESCRIPTION: SEQ ID NO:3:

| | | | | | | | | | | | | | | | |
|---|---|---|---|---|---|---|---|---|---|---|---|---|---|---|---|
| G | GAG | GTG | CAG | GAC | CTC | TTC | GAA | GCC | CAG | GGC | AAT | GAC | CGA | CTG | AAG | 46 |
| | Glu | Val | Gln | Asp | Leu | Phe | Glu | Ala | Gln | Gly | Asn | Asp | Arg | Leu | Lys | |
| | 1 | | | | 5 | | | | | 10 | | | | | 15 | |
| CTG | CTG | GTG | CTG | TAC | AGT | GGA | GAG | GAT | GAT | GAG | CTG | CTA | CAG | CGG | GCA | 94 |
| Leu | Leu | Val | Leu | Tyr | Ser | Gly | Glu | Asp | Asp | Glu | Leu | Leu | Gln | Arg | Ala | |
| | | | | 20 | | | | | 25 | | | | | 30 | | |
| GCT | GCC | GGG | GGC | TTG | GCC | ATG | CTT | ACC | TCC | ATG | CGG | CCC | ACG | CTC | TGC | 142 |
| Ala | Ala | Gly | Gly | Leu | Ala | Met | Leu | Thr | Ser | Met | Arg | Pro | Thr | Leu | Cys | |
| | | | 35 | | | | | 40 | | | | | 45 | | | |
| AGC | CGC | ATT | CCC | CAA | GTG | ACC | ACA | CAC | TGG | CTG | GAG | ATC | CTG | CAG | GCC | 190 |
| Ser | Arg | Ile | Pro | Gln | Val | Thr | Thr | His | Trp | Leu | Glu | Ile | Leu | Gln | Ala | |
| | | 50 | | | | | 55 | | | | | 60 | | | | |
| CTG | CTT | CTG | AGC | TCC | AAC | CAG | GAG | CTG | CAG | CAC | CGG | GGT | GCT | GTG | GTG | 238 |
| Leu | Leu | Leu | Ser | Ser | Asn | Gln | Glu | Leu | Gln | His | Arg | Gly | Ala | Val | Val | |
| | 65 | | | | | 70 | | | | | 75 | | | | | |
| GTG | CTG | AAC | ATG | GTG | GAG | GCC | TCG | AGG | GAG | ATT | GCC | AGC | ACC | CTG | ATG | 286 |
| Val | Leu | Asn | Met | Val | Glu | Ala | Ser | Arg | Glu | Ile | Ala | Ser | Thr | Leu | Met | |
| 80 | | | | | 85 | | | | | 90 | | | | | 95 | |
| GAG | AGT | GAG | ATG | ATG | GAG | ATC | TTG | TCA | GTG | CTA | GCT | AAG | GGT | GAC | CAC | 334 |
| Glu | Ser | Glu | Met | Met | Glu | Ile | Leu | Ser | Val | Leu | Ala | Lys | Gly | Asp | His | |
| | | | 100 | | | | | 105 | | | | | 110 | | | |
| AGC | CCT | GTC | ACA | AGG | GCT | GCT | GCA | GCC | TGC | CTG | GAC | AAA | GCA | GTG | GAA | 382 |
| Ser | Pro | Val | Thr | Arg | Ala | Ala | Ala | Ala | Cys | Leu | Asp | Lys | Ala | Val | Glu | |
| | | | 115 | | | | | 120 | | | | | 125 | | | |
| TAT | GGG | CTT | ATC | CAA | CCC | AAC | CAA | GAT | GGA | GAG | TGAGGGGGTT | | GTCCCTGGGC | | | 435 |
| Tyr | Gly | Leu | Ile | Gln | Pro | Asn | Gln | Asp | Gly | Glu | | | | | | |
| | | 130 | | | | | 135 | | | | | | | | | |
| CCAAGGCTCA | | TGCACACGCT | | ACCTATTGTG | | GCACGGAGAG | | TAAGGACGGA | | AGCAGCTTTG | | | | | | 495 |
| GCTGGTGGTG | | GCTGGCATGC | | CCAATACTCT | | TGCCCATCCT | | CGCTTGCTGC | | CCTAGGATGT | | | | | | 555 |

```
CCTCTGTTCT GAGTCAGCGG CCACGTTCAG TCACACAGCC CTGCTTGGCC AGCACTGCCT      615

GCAGCCTCAC TCAGAGGGGC CCTTTTTCTG TACTACTGTA GTCAGCTGGG AATGGGGAAG      675

GTGCATCCCA ACACAGCCTG TGGATCCTGG GGCATTTGGA AGGGCGCACA CATCAGCAGC      735

CTCACCAGCT GTGAGCCTGC TATCAGGCCT GCCCCTCCAA TAAAAGTGTG TAGAACTCCA      795

AAAAAAAAAA AAAAAAAAAA AAAAAAAAA A                                      826
```

(2) INFORMATION FOR SEQ ID NO:4:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:4:

```
Glu Val Gln Asp Leu Phe Glu Ala Gln Gly Asn Asp Arg Leu Lys Leu
 1               5                  10                  15

Leu Val Leu Tyr Ser Gly Glu Asp Glu Leu Leu Gln Arg Ala Ala
            20                  25                  30

Ala Gly Gly Leu Ala Met Leu Thr Ser Met Arg Pro Thr Leu Cys Ser
            35                  40                  45

Arg Ile Pro Gln Val Thr Thr His Trp Leu Glu Ile Leu Gln Ala Leu
        50                  55                  60

Leu Leu Ser Ser Asn Gln Glu Leu Gln His Arg Gly Ala Val Val Val
 65                 70                  75                  80

Leu Asn Met Val Glu Ala Ser Arg Glu Ile Ala Ser Thr Leu Met Glu
                85                  90                  95

Ser Glu Met Met Glu Ile Leu Ser Val Leu Ala Lys Gly Asp His Ser
               100                 105                 110

Pro Val Thr Arg Ala Ala Ala Ala Cys Leu Asp Lys Ala Val Glu Tyr
           115                 120                 125

Gly Leu Ile Gln Pro Asn Gln Asp Gly Glu
           130                 135
```

(2) INFORMATION FOR SEQ ID NO:5:

(i) SEQUENCE CHARACTERISTICS:
        (A) LENGTH: 722 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..559

(xi) SEQUENCE DESCRIPTION: SEQ ID NO:5:

```
G GAG AAG CCG CTG CAC GCC CTG CTG CAC GGC CGC GGG GTT TGC CTC         46
  Glu Lys Pro Leu His Ala Leu Leu His Gly Arg Gly Val Cys Leu
   1               5                  10                  15

AAC GAA AAG AGC TAC CGC GAG CAA GTC AAG ATC GAG AGA GAC TCC CGT       94
Asn Glu Lys Ser Tyr Arg Glu Gln Val Lys Ile Glu Arg Asp Ser Arg
                20                  25                  30

GAG CAC GAG GAG CCC ACC ACC TCT GAG ATG GCC GAG GAG ACC TAC TCC      142
Glu His Glu Glu Pro Thr Thr Ser Glu Met Ala Glu Glu Thr Tyr Ser
            35                  40                  45
```

| | | | | | | | | | | | | | | | | |
|---|---|---|---|---|---|---|---|---|---|---|---|---|---|---|---|---|
| CCC | AAG | ATC | TTC | CGG | CCC | AAA | CAC | ACC | CGC | ATC | TCC | GAG | CTG | AAG | GCT | 190 |
| Pro | Lys | Ile | Phe | Arg | Pro | Lys | His | Thr | Arg | Ile | Ser | Glu | Leu | Lys | Ala | |
| | | 50 | | | | 55 | | | | | 60 | | | | | |
| GAA | GCA | GTG | AAG | AAG | GAC | CGC | AGA | AAG | AAG | CTG | ACC | CAG | TCC | AAG | TTT | 238 |
| Glu | Ala | Val | Lys | Lys | Asp | Arg | Arg | Lys | Lys | Leu | Thr | Gln | Ser | Lys | Phe | |
| | 65 | | | | | 70 | | | | | 75 | | | | | |
| GTC | GGG | GGA | GCC | GAG | AAC | ACT | GCC | CAC | CCC | CGG | ATC | ATC | TCT | GAA | CCT | 286 |
| Val | Gly | Gly | Ala | Glu | Asn | Thr | Ala | His | Pro | Arg | Ile | Ile | Ser | Glu | Pro | |
| 80 | | | | | 85 | | | | | 90 | | | | | 95 | |
| GAG | ATG | AGA | CAG | GAG | TCT | GAG | CAG | GGC | CCC | TGC | CGC | AGA | CAC | ATG | GAG | 334 |
| Glu | Met | Arg | Gln | Glu | Ser | Glu | Gln | Gly | Pro | Cys | Arg | Arg | His | Met | Glu | |
| | | | | 100 | | | | | 105 | | | | | 110 | | |
| GCT | TCC | CTG | CAG | GAG | CTC | AAA | GCC | AGC | CCA | CGC | ATG | GTG | CCC | CGT | GCT | 382 |
| Ala | Ser | Leu | Gln | Glu | Leu | Lys | Ala | Ser | Pro | Arg | Met | Val | Pro | Arg | Ala | |
| | | | 115 | | | | | 120 | | | | | 125 | | | |
| GTG | TAC | CTG | CCC | AAT | TGT | GAC | CGC | AAA | GGA | TTC | TAC | AAG | AGA | AAG | CAG | 430 |
| Val | Tyr | Leu | Pro | Asn | Cys | Asp | Arg | Lys | Gly | Phe | Tyr | Lys | Arg | Lys | Gln | |
| | | 130 | | | | | 135 | | | | | 140 | | | | |
| TGC | AAA | CCT | TCC | CGT | GGC | CGC | AAG | CGT | GGC | ATC | TGC | TGG | TGC | GTG | GAC | 478 |
| Cys | Lys | Pro | Ser | Arg | Gly | Arg | Lys | Arg | Gly | Ile | Cys | Trp | Cys | Val | Asp | |
| | 145 | | | | | 150 | | | | | 155 | | | | | |
| AAG | TAC | GGG | ATG | AAG | CTG | CCA | GGC | ATG | GAG | TAC | GTT | GAC | GGG | GAC | TTT | 526 |
| Lys | Tyr | Gly | Met | Lys | Leu | Pro | Gly | Met | Glu | Tyr | Val | Asp | Gly | Asp | Phe | |
| 160 | | | | | 165 | | | | | 170 | | | | | 175 | |
| CAG | TGC | CAC | ACC | TTC | GAC | AGC | AGC | AAC | GTT | GAG | TGATGCGTCC | | CCCCCCAACC | | | 579 |
| Gln | Cys | His | Thr | Phe | Asp | Ser | Ser | Asn | Val | Glu | | | | | | |
| | | | | 180 | | | | | 185 | | | | | | | |
| TTTCCCTCAC | | CCCCTTCCAC | | CCCCAGCCCC | | GACTCCAGCC | | AGCGCCTCCC | | TCCACCCCAG | | | | | | 639 |
| GACGCCACTC | | ATTTCATCTC | | ATTTAAGGGA | | AAAATATATA | | TCTATCTATT | | TGAGGAAAAA | | | | | | 699 |
| AAAAAAAAAA | | AAAAAAAAAA | | AAA | | | | | | | | | | | | 722 |

( 2 ) INFORMATION FOR SEQ ID NO:6:

( i ) SEQUENCE CHARACTERISTICS:
        ( A ) LENGTH: 186 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Glu | Lys | Pro | Leu | His | Ala | Leu | Leu | His | Gly | Arg | Gly | Val | Cys | Leu | Asn |
| 1 | | | | 5 | | | | | 10 | | | | | 15 |
| Glu | Lys | Ser | Tyr | Arg | Glu | Gln | Val | Lys | Ile | Glu | Arg | Asp | Ser | Arg | Glu |
| | | | 20 | | | | | 25 | | | | 30 | | | |
| His | Glu | Glu | Pro | Thr | Thr | Ser | Glu | Met | Ala | Glu | Thr | Tyr | Ser | Pro |
| | | 35 | | | | | 40 | | | | | 45 | | |
| Lys | Ile | Phe | Arg | Pro | Lys | His | Thr | Arg | Ile | Ser | Glu | Leu | Lys | Ala | Glu |
| | | 50 | | | | 55 | | | | | 60 | | | | |
| Ala | Val | Lys | Lys | Asp | Arg | Arg | Lys | Lys | Leu | Thr | Gln | Ser | Lys | Phe | Val |
| 65 | | | | | 70 | | | | | 75 | | | | | 80 |
| Gly | Gly | Ala | Glu | Asn | Thr | Ala | His | Pro | Arg | Ile | Ile | Ser | Glu | Pro | Glu |
| | | | | 85 | | | | | 90 | | | | | 95 | |
| Met | Arg | Gln | Glu | Ser | Glu | Gln | Gly | Pro | Cys | Arg | Arg | His | Met | Glu | Ala |
| | | | 100 | | | | | 105 | | | | | 110 | | |
| Ser | Leu | Gln | Glu | Leu | Lys | Ala | Ser | Pro | Arg | Met | Val | Pro | Arg | Ala | Val |
| | | 115 | | | | | 120 | | | | | 125 | | | |
| Tyr | Leu | Pro | Asn | Cys | Asp | Arg | Lys | Gly | Phe | Tyr | Lys | Arg | Lys | Gln | Cys |
| | 130 | | | | | 135 | | | | | 140 | | | | |

| Lys | Pro | Ser | Arg | Gly | Arg | Lys | Arg | Gly | Ile | Cys | Trp | Cys | Val | Asp | Lys |
| 145 | | | | | 150 | | | | | 155 | | | | | 160 |

| Tyr | Gly | Met | Lys | Leu | Pro | Gly | Met | Glu | Tyr | Val | Asp | Gly | Asp | Phe | Gln |
| | | | | 165 | | | | | 170 | | | | | 175 | |

| Cys | His | Thr | Phe | Asp | Ser | Ser | Asn | Val | Glu |
| | | | 180 | | | | 185 | | |

( 2 ) INFORMATION FOR SEQ ID NO:7:

( i ) SEQUENCE CHARACTERISTICS:
        ( A ) LENGTH: 1023 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 57..875

( x i ) SEQUENCE DESCRIPTION: SEQ ID NO:7:

```
CCCTGCACTC TCGCTCTCCT GCCCCACCCC GAGGTAAAGG GGGCGACTAA GAGAAG                    56
```

| ATG | GTG | TTG | CTC | ACC | GCG | GTC | CTC | CTG | CTG | CTG | GCC | GCC | TAT | GCG | GGG | 104 |
| Met | Val | Leu | Leu | Thr | Ala | Val | Leu | Leu | Leu | Leu | Ala | Ala | Tyr | Ala | Gly | |
| 1 | | | | 5 | | | | | 10 | | | | | 15 | | |

| CCG | GCC | CAG | AGC | CTG | GGC | TCC | TTC | GTG | CAC | TGC | GAG | CCC | TGC | GAC | GAG | 152 |
| Pro | Ala | Gln | Ser | Leu | Gly | Ser | Phe | Val | His | Cys | Glu | Pro | Cys | Asp | Glu | |
| | | | 20 | | | | | 25 | | | | | 30 | | | |

| AAA | GCC | CTC | TCC | ATG | TGC | CCC | CCC | AGC | CCC | CTG | GGC | TGC | GAG | CTG | GTC | 200 |
| Lys | Ala | Leu | Ser | Met | Cys | Pro | Pro | Ser | Pro | Leu | Gly | Cys | Glu | Leu | Val | |
| | | | 35 | | | | | 40 | | | | | 45 | | | |

| AAG | GAG | CCG | GGC | TGC | GGC | TGC | TGC | ATG | ACC | TGC | GCC | CTG | GCC | GAG | GGG | 248 |
| Lys | Glu | Pro | Gly | Cys | Gly | Cys | Cys | Met | Thr | Cys | Ala | Leu | Ala | Glu | Gly | |
| | 50 | | | | | 55 | | | | | 60 | | | | | |

| CAG | TCG | TGC | GGC | GTC | TAC | ACC | GAG | CGC | TGC | GCC | CAG | GGG | CTG | CGC | TGC | 296 |
| Gln | Ser | Cys | Gly | Val | Tyr | Thr | Glu | Arg | Cys | Ala | Gln | Gly | Leu | Arg | Cys | |
| 65 | | | | | 70 | | | | | 75 | | | | | 80 | |

| CTC | CCC | CGG | CAG | GAC | GAG | GAG | AAG | CCG | CTG | CAC | GCC | CTG | CTG | CAC | GGC | 344 |
| Leu | Pro | Arg | Gln | Asp | Glu | Glu | Lys | Pro | Leu | His | Ala | Leu | Leu | His | Gly | |
| | | | | 85 | | | | | 90 | | | | | 95 | | |

| CGC | GGG | GTT | TGC | CTC | AAC | GAA | AAG | AGC | TAC | CGC | GAG | CAA | GTC | AAG | ATC | 392 |
| Arg | Gly | Val | Cys | Leu | Asn | Glu | Lys | Ser | Tyr | Arg | Glu | Gln | Val | Lys | Ile | |
| | | | 100 | | | | | 105 | | | | | 110 | | | |

| GAG | AGA | GAC | TCC | CGT | GAG | CAC | GAG | GAG | CCC | ACC | ACC | TCT | GAG | ATG | GCC | 440 |
| Glu | Arg | Asp | Ser | Arg | Glu | His | Glu | Glu | Pro | Thr | Thr | Ser | Glu | Met | Ala | |
| | | 115 | | | | | 120 | | | | | 125 | | | | |

| GAG | GAG | ACC | TAC | TCC | CCC | AAG | ATC | TTC | CGG | CCC | AAA | CAC | ACC | CGC | ATC | 488 |
| Glu | Glu | Thr | Tyr | Ser | Pro | Lys | Ile | Phe | Arg | Pro | Lys | His | Thr | Arg | Ile | |
| | | 130 | | | | | 135 | | | | | 140 | | | | |

| TCC | GAG | CTG | AAG | GCT | GAA | GCA | GTG | AAG | AAG | GAC | CGC | AGA | AAG | AAG | CTG | 536 |
| Ser | Glu | Leu | Lys | Ala | Glu | Ala | Val | Lys | Lys | Asp | Arg | Arg | Lys | Lys | Leu | |
| 145 | | | | | 150 | | | | | 155 | | | | | 160 | |

| ACC | CAG | TCC | AAG | TTT | GTC | GGG | GGA | GCC | GAG | AAC | ACT | GCC | CAC | CCC | CGG | 584 |
| Thr | Gln | Ser | Lys | Phe | Val | Gly | Gly | Ala | Glu | Asn | Thr | Ala | His | Pro | Arg | |
| | | | | 165 | | | | | 170 | | | | | 175 | | |

| ATC | ATC | TCT | GCA | CCT | GAG | ATG | AGA | CAG | GAG | TCT | GAG | CAG | GGC | CCC | TGC | 632 |
| Ile | Ile | Ser | Ala | Pro | Glu | Met | Arg | Gln | Glu | Ser | Glu | Gln | Gly | Pro | Cys | |
| | | | 180 | | | | 185 | | | | | 190 | | | | |

| CGC | AGA | CAC | ATG | GAG | GCT | TCC | CTG | CAG | GAG | CTC | AAA | GCC | AGC | CCA | CGC | 680 |

```
Arg  Arg  His  Met  Glu  Ala  Ser  Leu  Gln  Glu  Leu  Lys  Ala  Ser  Pro  Arg
          195                200                     205

ATG  GTG  CCC  CGT  GCT  GTG  TAC  CTG  CCC  AAT  TGT  GAC  CGC  AAA  GGA  TTC        728
Met  Val  Pro  Arg  Ala  Val  Tyr  Leu  Pro  Asn  Cys  Asp  Arg  Lys  Gly  Phe
     210                     215                     220

TAC  AAG  AGA  AAG  CAG  TGC  AAA  CCT  TCC  CGT  GGC  CGC  AAG  CGT  GGC  ATC        776
Tyr  Lys  Arg  Lys  Gln  Cys  Lys  Pro  Ser  Arg  Gly  Arg  Lys  Arg  Gly  Ile
225                      230                     235                      240

TGC  TGG  TGC  GTG  GAC  AAG  TAC  GGG  ATG  AAG  CTG  CCA  GGC  ATG  GAG  TAC        824
Cys  Trp  Cys  Val  Asp  Lys  Tyr  Gly  Met  Lys  Leu  Pro  Gly  Met  Glu  Tyr
                    245                     250                     255

GTT  GAC  GGG  GAC  TTT  CAG  TGC  CAC  ACC  TTC  GAC  AGC  AGC  AAC  GTT  GAG        872
Val  Asp  Gly  Asp  Phe  Gln  Cys  His  Thr  Phe  Asp  Ser  Ser  Asn  Val  Glu
                    260                     265                     270

TGATGCGTCC  CCCCCAACC  TTTCCTCAC  CCCTCCCAC  CCCCAGCCCC  GACTCCAGCC                    932

AGCGCCTCCC  TCCACCCCAG  GACGCCACTC  ATTTCATCTC  ATTAAGGGA  AAAATATATA                  992

TCTATCTATT  TGAAAAAAAA  AAAAAAACC  C                                                  1023
```

( 2 ) INFORMATION FOR SEQ ID NO:8:

( i ) SEQUENCE CHARACTERISTICS:
        ( A ) LENGTH: 272 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Val  Leu  Leu  Thr  Ala  Val  Leu  Leu  Leu  Ala  Ala  Tyr  Ala  Gly
 1                    5                    10                       15

Pro  Ala  Gln  Ser  Leu  Gly  Ser  Phe  Val  His  Cys  Glu  Pro  Cys  Asp  Glu
               20                     25                      30

Lys  Ala  Leu  Ser  Met  Cys  Pro  Pro  Ser  Pro  Leu  Gly  Cys  Glu  Leu  Val
                35                     40                      45

Lys  Glu  Pro  Gly  Cys  Gly  Cys  Cys  Met  Thr  Cys  Ala  Leu  Ala  Glu  Gly
     50                     55                      60

Gln  Ser  Cys  Gly  Val  Tyr  Thr  Glu  Arg  Cys  Ala  Gln  Gly  Leu  Arg  Cys
65                       70                      75                      80

Leu  Pro  Arg  Gln  Asp  Glu  Glu  Lys  Pro  Leu  His  Ala  Leu  Leu  His  Gly
                    85                     90                      95

Arg  Gly  Val  Cys  Leu  Asn  Glu  Lys  Ser  Tyr  Arg  Glu  Gln  Val  Lys  Ile
                    100                    105                     110

Glu  Arg  Asp  Ser  Arg  Glu  His  Glu  Glu  Pro  Thr  Thr  Ser  Glu  Met  Ala
                    115                    120                     125

Glu  Glu  Thr  Tyr  Ser  Pro  Lys  Ile  Phe  Arg  Pro  Lys  His  Thr  Arg  Ile
     130                    135                    140

Ser  Glu  Leu  Lys  Ala  Glu  Ala  Val  Lys  Lys  Asp  Arg  Arg  Lys  Lys  Leu
145                      150                    155                     160

Thr  Gln  Ser  Lys  Phe  Val  Gly  Gly  Ala  Glu  Asn  Thr  Ala  His  Pro  Arg
                    165                    170                     175

Ile  Ile  Ser  Ala  Pro  Glu  Met  Arg  Gln  Glu  Ser  Glu  Gln  Gly  Pro  Cys
                    180                    185                     190

Arg  Arg  His  Met  Glu  Ala  Ser  Leu  Gln  Glu  Leu  Lys  Ala  Ser  Pro  Arg
          195                    200                     205

Met  Val  Pro  Arg  Ala  Val  Tyr  Leu  Pro  Asn  Cys  Asp  Arg  Lys  Gly  Phe
     210                    215                     220

Tyr  Lys  Arg  Lys  Gln  Cys  Lys  Pro  Ser  Arg  Gly  Arg  Lys  Arg  Gly  Ile
```

|  |  |  |  | 225 |  |  |  |  | 230 |  |  |  |  | 235 |  |  |  |  | 240 |
|---|---|---|---|---|---|---|---|---|---|---|---|---|---|---|---|---|---|---|---|

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
            260             265                 270

( 2 ) INFORMATION FOR SEQ ID NO:9:

( i ) SEQUENCE CHARACTERISTICS:
          ( A ) LENGTH: 1694 base pairs
          ( B ) TYPE: nucleic acid
          ( C ) STRANDEDNESS: double
          ( D ) TOPOLOGY: linear ( i i ) MOLECULE TYPE: cDNA ( i i i ) HYPOTHETICAL: NO ( i x ) FEATURE:
          ( A ) NAME/KEY: CDS
          ( B ) LOCATION: 2..931

( x i ) SEQUENCE DESCRIPTION: SEQ ID NO:9:

```
C  TCT  CTC  AAG  GCC  AAC  ATC  CCT  GAG  GTG  AAA  GCT  GTC  CTC  AAC  ACC      46
   Ser  Leu  Lys  Ala  Asn  Ile  Pro  Glu  Val  Glu  Ala  Val  Leu  Asn  Thr
   1              5                   10                  15

GAC  AGG  AGT  TTG  GTG  TGT  GAT  GGG  AAG  AGG  GGC  TTA  TTA  ACT  CGT  CTG      94
Asp  Arg  Ser  Leu  Val  Cys  Asp  Gly  Lys  Arg  Gly  Leu  Leu  Thr  Arg  Leu
                    20                  25                  30

CTG  CAG  GTC  ATG  AAG  AAG  GAG  CCA  GCA  GAG  TCG  TCT  TTC  AGG  TTT  TGG     142
Leu  Gln  Val  Met  Lys  Lys  Glu  Pro  Ala  Glu  Ser  Ser  Phe  Arg  Phe  Trp
              35                  40                  45

CAA  GCT  CGG  GCT  GTG  GAG  AGT  TTC  CTC  CGA  GGG  ACC  ACC  TCC  TAT  GCA     190
Gln  Ala  Arg  Ala  Val  Glu  Ser  Phe  Leu  Arg  Gly  Thr  Thr  Ser  Tyr  Ala
         50                  55                  60

GAC  CAG  ATG  TTC  CTG  CTG  AAG  CGA  GGC  CTC  TTG  GAG  CAC  ATC  CTT  TAC     238
Asp  Gln  Met  Phe  Leu  Leu  Lys  Arg  Gly  Leu  Leu  Glu  His  Ile  Leu  Tyr
    65                  70                  75

TGC  ATT  GTG  GAC  AGC  GAG  TGT  AAG  TCA  AGG  GAT  GTG  CTC  CAG  AGT  TAC     286
Cys  Ile  Val  Asp  Ser  Glu  Cys  Lys  Ser  Arg  Asp  Val  Leu  Gln  Ser  Tyr
80                   85                  90                           95

TTT  GAC  CTC  CTG  GGG  GAG  CTG  ATG  AAG  TTC  AAC  GTT  GAT  GCA  TTC  AAG     334
Phe  Asp  Leu  Leu  Gly  Glu  Leu  Met  Lys  Phe  Asn  Val  Asp  Ala  Phe  Lys
                    100                 105                 110

AGA  TTC  AAT  AAA  TAT  ATC  AAC  ACC  GAT  GCA  AAG  TTC  CAG  GTA  TTC  CTG     382
Arg  Phe  Asn  Lys  Tyr  Ile  Asn  Thr  Asp  Ala  Lys  Phe  Gln  Val  Phe  Leu
              115                 120                 125

AAG  CAG  ATC  AAC  AGC  TCC  CTG  GTG  GAC  TCC  AAC  ATG  CTG  GTG  CGC  TGT     430
Lys  Gln  Ile  Asn  Ser  Ser  Leu  Val  Asp  Ser  Asn  Met  Leu  Val  Arg  Cys
         130                 135                 140

GTC  ACT  CTG  TCC  CTG  GAC  CGA  TTT  GAA  AAC  CAG  GTG  GAT  ATG  AAA  GTT     478
Val  Thr  Leu  Ser  Leu  Asp  Arg  Phe  Glu  Asn  Gln  Val  Asp  Met  Lys  Val
    145                 150                 155

GCC  GAG  GTA  CTG  TCT  GAA  TGC  CGC  CTG  CTC  GCC  TAC  ATA  TCC  CAG  GTG     526
Ala  Glu  Val  Leu  Ser  Glu  Cys  Arg  Leu  Leu  Ala  Tyr  Ile  Ser  Gln  Val
160                 165                 170                     175

CCC  ACG  CAG  ATG  TCC  TTC  CTC  TTC  CGC  CTC  ATC  AAC  ATC  ATC  CAC  GTG     574
Pro  Thr  Gln  Met  Ser  Phe  Leu  Phe  Arg  Leu  Ile  Asn  Ile  Ile  His  Val
                    180                 185                 190

CAG  ACG  CTG  ACC  CAG  GAG  AAC  GTC  AGC  TGC  CTC  AAC  ACC  AGC  CTG  GTG     622
Gln  Thr  Leu  Thr  Gln  Glu  Asn  Val  Ser  Cys  Leu  Asn  Thr  Ser  Leu  Val
              195                 200                 205

ATC  CTG  ATG  CTG  GCC  CGA  CGG  AAA  GAG  CGG  CTG  CCC  CTG  TAC  CTG  CGG     670
```

```
        Ile  Leu  Met  Leu  Ala  Arg  Arg  Lys  Glu  Arg  Leu  Pro  Leu  Tyr  Leu  Arg
                  210                      215                      220

CTG  CTG  CAG  CGG  ATG  GAG  CAC  AGC  AAG  AAG  TAC  CCC  GGC  TTC  CTG  CTC                 718
Leu  Leu  Gln  Arg  Met  Glu  His  Ser  Lys  Lys  Tyr  Pro  Gly  Phe  Leu  Leu
          225                      230                      235

AAC  AAC  TTC  CAC  AAC  CTG  CTG  CGC  TTC  TGG  CAG  CAG  CAC  TAC  CTG  CAC                 766
Asn  Asn  Phe  His  Asn  Leu  Leu  Arg  Phe  Trp  Gln  Gln  His  Tyr  Leu  His
240                      245                      250                           255

AAG  GAC  AAG  GAC  AGC  ACC  TGC  CTA  GAG  AAC  AGC  TCC  TGC  ATC  AGC  TTC                 814
Lys  Asp  Lys  Asp  Ser  Thr  Cys  Leu  Glu  Asn  Ser  Ser  Cys  Ile  Ser  Phe
                         260                      265                      270

TCA  TAC  TGG  AAG  GAG  ACA  GTG  TCC  ATC  CTG  TTG  AAC  CCG  GAC  CGG  CAG                 862
Ser  Tyr  Trp  Lys  Glu  Thr  Val  Ser  Ile  Leu  Leu  Asn  Pro  Asp  Arg  Gln
               275                      280                      285

TCA  CCC  TCT  GCT  CTC  GTT  AGC  TAC  ATT  GAG  GAG  CCC  TAC  ATG  GAC  ATA                 910
Ser  Pro  Ser  Ala  Leu  Val  Ser  Tyr  Ile  Glu  Glu  Pro  Tyr  Met  Asp  Ile
          290                      295                      300

GAC  AGG  GAC  TTC  ACT  GAG  GAG  TGACCTTGGG  CCAGGCCTCG  GGAGGCTGCT                           961
Asp  Arg  Asp  Phe  Thr  Glu  Glu
          305                 310

GGGCCAGTGT  GGGTGAGCGT  GGGTACGATG  CCACACGCCC  TGCCCTGTTC  CCGTTCCTCC                         1021

CTGCTGCTCT  CTGCCTGCCC  CAGGTCTTTG  GGTACAGGCT  TGGTGGGAGG  GAAGTCCTAG                          1081

AAGCCCTTGG  TCCCCCTGGG  TCTGAGGGCC  CTAGGTCATG  GAGAGCCTCA  GTCCCCATAA                          1141

TGAGGACAGG  GTACCATGCC  CACCTTTCCT  TCAGAACCCT  GGGGCCCAGG  GCCACCCAGA                          1201

GGTAAGAGGA  CATTTAGCAT  TAGCTCTGTG  TGAGCTCCTG  CCGGTTTCTT  GGCTGTCAGT                          1261

CAGTCCCAGA  GTGGGGAGGA  AGATATGGGT  GACCCCCACC  CCCCATCTGT  GAGCCAAGCC                          1321

TCCCTTGTCC  CTGGCCTTTG  GACCCAGGCA  AAGGCTTCTG  AGCCCTGGGC  AGGGGTGGTG                          1381

GGTACCAGAG  AATGCTGCCT  TCCCCCAAGC  CTGCCCCTCT  GCCTCATTTT  CCTGTAGCTC                          1441

CTCTGGTTCT  GTTTGCTCAT  TGGCCGCTGT  GTTCATCCAA  GGGGGTTCTC  CCAGAAGTGA                          1501

GGGGCCTTTC  CCTCCATCCC  TTGGGGCACG  GGGCAGCTGT  GCCTGCCCTG  CCTCTGCCTG                          1561

AGGCAGCCGC  TCCTGCCTGA  GCCTGGACAT  GGGGCCCTTC  CTTGTGTTGC  CAATTTATTA                          1621

ACAGCAAATA  AACCAATTAA  ATGGAGACTA  TTAAATAACT  TTATTTAAA   AATGAAAAAA                          1681

AAAAAAAAAA  AAA                                                                                1694

( 2 ) INFORMATION FOR SEQ ID NO:10:

( i ) SEQUENCE CHARACTERISTICS:
                ( A ) LENGTH: 310 amino acids
                ( B ) TYPE: amino acid
                ( D ) TOPOLOGY: linear ( i i ) MOLECULE TYPE: protein ( x i ) SEQUENCE DESCRIPTION: SEQ ID NO:10:

Ser  Leu  Lys  Ala  Asn  Ile  Pro  Glu  Val  Glu  Ala  Val  Leu  Asn  Thr  Asp
 1                  5                      10                      15

Arg  Ser  Leu  Val  Cys  Asp  Gly  Lys  Arg  Gly  Leu  Leu  Thr  Arg  Leu  Leu
               20                      25                      30

Gln  Val  Met  Lys  Lys  Glu  Pro  Ala  Glu  Ser  Ser  Phe  Arg  Phe  Trp  Gln
          35                      40                      45

Ala  Arg  Ala  Val  Glu  Ser  Phe  Leu  Arg  Gly  Thr  Thr  Ser  Tyr  Ala  Asp
     50                      55                      60

Gln  Met  Phe  Leu  Leu  Lys  Arg  Gly  Leu  Leu  Glu  His  Ile  Leu  Tyr  Cys
65                      70                      75                          80
```

| Ile | Val | Asp | Ser | Glu | Cys | Lys | Ser | Arg | Asp | Val | Leu | Gln | Ser | Tyr | Phe |
|---|---|---|---|---|---|---|---|---|---|---|---|---|---|---|---|
| | | | | 85 | | | | 90 | | | | | | 95 | |

| Asp | Leu | Leu | Gly | Glu | Leu | Met | Lys | Phe | Asn | Val | Asp | Ala | Phe | Lys | Arg |
|---|---|---|---|---|---|---|---|---|---|---|---|---|---|---|---|
| | | | 100 | | | | 105 | | | | | 110 | | | |

| Phe | Asn | Lys | Tyr | Ile | Asn | Thr | Asp | Ala | Lys | Phe | Gln | Val | Phe | Leu | Lys |
|---|---|---|---|---|---|---|---|---|---|---|---|---|---|---|---|
| | | 115 | | | | | 120 | | | | | 125 | | | |

| Gln | Ile | Asn | Ser | Ser | Leu | Val | Asp | Ser | Asn | Met | Leu | Val | Arg | Cys | Val |
|---|---|---|---|---|---|---|---|---|---|---|---|---|---|---|---|
| | 130 | | | | | 135 | | | | | 140 | | | | |

| Thr | Leu | Ser | Leu | Asp | Arg | Phe | Glu | Asn | Gln | Val | Asp | Met | Lys | Val | Ala |
|---|---|---|---|---|---|---|---|---|---|---|---|---|---|---|---|
| 145 | | | | | 150 | | | | | 155 | | | | | 160 |

| Glu | Val | Leu | Ser | Glu | Cys | Arg | Leu | Leu | Ala | Tyr | Ile | Ser | Gln | Val | Pro |
|---|---|---|---|---|---|---|---|---|---|---|---|---|---|---|---|
| | | | | 165 | | | | | 170 | | | | | 175 | |

| Thr | Gln | Met | Ser | Phe | Leu | Phe | Arg | Leu | Ile | Asn | Ile | Ile | His | Val | Gln |
|---|---|---|---|---|---|---|---|---|---|---|---|---|---|---|---|
| | | | 180 | | | | | 185 | | | | | 190 | | |

| Thr | Leu | Thr | Gln | Glu | Asn | Val | Ser | Cys | Leu | Asn | Thr | Ser | Leu | Val | Ile |
|---|---|---|---|---|---|---|---|---|---|---|---|---|---|---|---|
| | | 195 | | | | | 200 | | | | | 205 | | | |

| Leu | Met | Leu | Ala | Arg | Arg | Lys | Glu | Arg | Leu | Pro | Leu | Tyr | Leu | Arg | Leu |
|---|---|---|---|---|---|---|---|---|---|---|---|---|---|---|---|
| | 210 | | | | | 215 | | | | | 220 | | | | |

| Leu | Gln | Arg | Met | Glu | His | Ser | Lys | Lys | Tyr | Pro | Gly | Phe | Leu | Leu | Asn |
|---|---|---|---|---|---|---|---|---|---|---|---|---|---|---|---|
| 225 | | | | | 230 | | | | | 235 | | | | | 240 |

| Asn | Phe | His | Asn | Leu | Leu | Arg | Phe | Trp | Gln | Gln | His | Tyr | Leu | His | Lys |
|---|---|---|---|---|---|---|---|---|---|---|---|---|---|---|---|
| | | | | 245 | | | | | 250 | | | | | 255 | |

| Asp | Lys | Asp | Ser | Thr | Cys | Leu | Glu | Asn | Ser | Ser | Cys | Ile | Ser | Phe | Ser |
|---|---|---|---|---|---|---|---|---|---|---|---|---|---|---|---|
| | | | 260 | | | | | 265 | | | | | 270 | | |

| Tyr | Trp | Lys | Glu | Thr | Val | Ser | Ile | Leu | Leu | Asn | Pro | Asp | Arg | Gln | Ser |
|---|---|---|---|---|---|---|---|---|---|---|---|---|---|---|---|
| | | 275 | | | | | 280 | | | | | 285 | | | |

| Pro | Ser | Ala | Leu | Val | Ser | Tyr | Ile | Glu | Glu | Pro | Tyr | Met | Asp | Ile | Asp |
|---|---|---|---|---|---|---|---|---|---|---|---|---|---|---|---|
| | 290 | | | | | 295 | | | | | 300 | | | | |

| Arg | Asp | Phe | Thr | Glu | Glu |
|---|---|---|---|---|---|
| 305 | | | | | 310 |

( 2 ) INFORMATION FOR SEQ ID NO:11:

( i ) SEQUENCE CHARACTERISTICS:
        ( A ) LENGTH: 2735 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..1822

( x i ) SEQUENCE DESCRIPTION: SEQ ID NO:11:

| G | GAG | ATC | AGT | CGG | AAG | GTG | TAC | AAG | GGA | ATG | TTA | GAC | CTC | CTC | AAG | 46 |
|---|---|---|---|---|---|---|---|---|---|---|---|---|---|---|---|---|
| | Glu | Ile | Ser | Arg | Lys | Val | Tyr | Lys | Gly | Met | Leu | Asp | Leu | Leu | Lys | |
| | 1 | | | | 5 | | | | | 10 | | | | | 15 | |

| TGT | ACA | GTC | CTC | AGC | TTG | GAG | CAG | TCC | TAT | GCC | CAC | GCG | GGT | CTG | GGT | 94 |
|---|---|---|---|---|---|---|---|---|---|---|---|---|---|---|---|---|
| Cys | Thr | Val | Leu | Ser | Leu | Glu | Gln | Ser | Tyr | Ala | His | Ala | Gly | Leu | Gly | |
| | | | | 20 | | | | | 25 | | | | | 30 | | |

| GGC | ATG | GCC | AGC | ATC | TTT | GGG | CTT | TTG | GAG | ATT | GCC | CAG | ACC | CAC | TAC | 142 |
|---|---|---|---|---|---|---|---|---|---|---|---|---|---|---|---|---|
| Gly | Met | Ala | Ser | Ile | Phe | Gly | Leu | Leu | Glu | Ile | Ala | Gln | Thr | His | Tyr | |
| | | | 35 | | | | | 40 | | | | | 45 | | | |

| TAT | AGT | AAA | GAA | CCA | GAC | AAG | CGG | AAG | AGA | AGT | CCA | ACA | GAA | AGT | GTA | 190 |
|---|---|---|---|---|---|---|---|---|---|---|---|---|---|---|---|---|
| Tyr | Ser | Lys | Glu | Pro | Asp | Lys | Arg | Lys | Arg | Ser | Pro | Thr | Glu | Ser | Val | |
| | | 50 | | | | | 55 | | | | | 60 | | | | |

| | | | | | | | | | | | | | | | | |
|---|---|---|---|---|---|---|---|---|---|---|---|---|---|---|---|---|
| AAT | ACC | CCA | GTT | GGC | AAG | GAT | CCT | GGC | CTA | GCT | GGG | CGG | GGG | GAC | CCA | 238 |
| Asn | Thr | Pro | Val | Gly | Lys | Asp | Pro | Gly | Leu | Ala | Gly | Arg | Gly | Asp | Pro | |
| | 65 | | | | 70 | | | | | 75 | | | | | | |
| AAG | GCT | ATG | GCA | CAA | CTG | AGA | GTT | CCA | CAA | CTG | GGA | CCT | CGG | GCA | CCA | 286 |
| Lys | Ala | Met | Ala | Gln | Leu | Arg | Val | Pro | Gln | Leu | Gly | Pro | Arg | Ala | Pro | |
| 80 | | | | | 85 | | | | | 90 | | | | | 95 | |
| AGT | GCC | ACA | GGA | AAG | GGT | CCT | AAG | GAA | CTG | GAC | ACC | AGA | AGT | TTA | AAG | 334 |
| Ser | Ala | Thr | Gly | Lys | Gly | Pro | Lys | Glu | Leu | Asp | Thr | Arg | Ser | Leu | Lys | |
| | | | | 100 | | | | | 105 | | | | | 110 | | |
| GAA | GAA | AAT | TTT | ATA | GCA | TCT | ATT | GGG | CCT | GAA | GTA | ATC | AAA | CCT | GTC | 382 |
| Glu | Glu | Asn | Phe | Ile | Ala | Ser | Ile | Gly | Pro | Glu | Val | Ile | Lys | Pro | Val | |
| | | | 115 | | | | | 120 | | | | | 125 | | | |
| TTT | GAC | CTT | GGT | GAG | ACA | GAG | GAG | AAA | AAG | TCC | CAG | ATC | AGC | GCA | GAC | 430 |
| Phe | Asp | Leu | Gly | Glu | Thr | Glu | Glu | Lys | Lys | Ser | Gln | Ile | Ser | Ala | Asp | |
| | | 130 | | | | | 135 | | | | | 140 | | | | |
| AGT | GGT | GTG | AGC | CTG | ACG | TCT | AGT | TCC | CAG | AGG | ACT | GAT | CAA | GAC | TCT | 478 |
| Ser | Gly | Val | Ser | Leu | Thr | Ser | Ser | Ser | Gln | Arg | Thr | Asp | Gln | Asp | Ser | |
| | 145 | | | | | 150 | | | | | 155 | | | | | |
| GTC | ATC | GGC | GTG | AGT | CCA | GCT | GTT | ATG | ATC | CGC | AGC | TCA | AGT | CAG | GAT | 526 |
| Val | Ile | Gly | Val | Ser | Pro | Ala | Val | Met | Ile | Arg | Ser | Ser | Ser | Gln | Asp | |
| 160 | | | | | 165 | | | | | 170 | | | | | 175 | |
| TCT | GAA | GTT | AGC | ACC | GTG | GTG | AGT | AAT | AGC | TCT | GGA | GAG | ACC | CTT | GGA | 574 |
| Ser | Glu | Val | Ser | Thr | Val | Val | Ser | Asn | Ser | Ser | Gly | Glu | Thr | Leu | Gly | |
| | | | | 180 | | | | | 185 | | | | | 190 | | |
| GCT | GAC | AGT | GAC | TTG | AGC | AGC | AAT | GCA | GGT | GAT | GGA | CCA | GGT | GGC | GAG | 622 |
| Ala | Asp | Ser | Asp | Leu | Ser | Ser | Asn | Ala | Gly | Asp | Gly | Pro | Gly | Gly | Glu | |
| | | | 195 | | | | | 200 | | | | | 205 | | | |
| GGC | AGT | GTT | CAC | CTG | GCA | AGC | TCT | CGG | GGC | ACT | TTG | TCT | GAT | AGT | GAA | 670 |
| Gly | Ser | Val | His | Leu | Ala | Ser | Ser | Arg | Gly | Thr | Leu | Ser | Asp | Ser | Glu | |
| | | 210 | | | | | 215 | | | | | 220 | | | | |
| ATT | GAG | ACC | AAC | TCT | GCC | ACA | AGC | ACC | ATC | TTT | GGT | AAA | GCC | CAC | AGC | 718 |
| Ile | Glu | Thr | Asn | Ser | Ala | Thr | Ser | Thr | Ile | Phe | Gly | Lys | Ala | His | Ser | |
| | 225 | | | | | 230 | | | | | 235 | | | | | |
| TTG | AAG | CCA | AGC | ATA | AAG | GAG | AAG | CTG | GCA | GGC | AGC | CCC | ATT | CGT | ACT | 766 |
| Leu | Lys | Pro | Ser | Ile | Lys | Glu | Lys | Leu | Ala | Gly | Ser | Pro | Ile | Arg | Thr | |
| 240 | | | | | 245 | | | | | 250 | | | | | 255 | |
| TCT | GAA | GAT | GTG | AGC | CAG | CGA | GTC | TAT | CTC | TAT | GAG | GGA | CTC | CTA | GGC | 814 |
| Ser | Glu | Asp | Val | Ser | Gln | Arg | Val | Tyr | Leu | Tyr | Glu | Gly | Leu | Leu | Gly | |
| | | | | 260 | | | | | 265 | | | | | 270 | | |
| AAA | GAG | CGT | TCT | ACT | TTA | TGG | GAC | CAA | ATG | CAA | TTC | TGG | GAA | GAT | GCC | 862 |
| Lys | Glu | Arg | Ser | Thr | Leu | Trp | Asp | Gln | Met | Gln | Phe | Trp | Glu | Asp | Ala | |
| | | | 275 | | | | | 280 | | | | | 285 | | | |
| TTC | TTA | GAT | GCT | GTG | ATG | TTG | GAG | AGA | GAA | GGG | ATG | GGT | ATG | GAC | CAG | 910 |
| Phe | Leu | Asp | Ala | Val | Met | Leu | Glu | Arg | Glu | Gly | Met | Gly | Met | Asp | Gln | |
| | | | 290 | | | | | 295 | | | | | 300 | | | |
| GGT | CCC | CAG | GAA | ATG | ATC | GAC | AGG | TAC | CTG | TCC | CTT | GGA | GAA | CAT | GAC | 958 |
| Gly | Pro | Gln | Glu | Met | Ile | Asp | Arg | Tyr | Leu | Ser | Leu | Gly | Glu | His | Asp | |
| | 305 | | | | | 310 | | | | | 315 | | | | | |
| CGG | AAG | CGC | CTG | GAA | GAT | GAT | GAA | GAT | CGC | TTG | CTG | GCC | ACA | CTT | CTG | 1006 |
| Arg | Lys | Arg | Leu | Glu | Asp | Asp | Glu | Asp | Arg | Leu | Leu | Ala | Thr | Leu | Leu | |
| 320 | | | | | 325 | | | | | 330 | | | | | 335 | |
| CAC | AAC | CTC | ATC | TCC | TAC | ATG | CTG | CTG | ATG | AAG | GTA | AAT | AAG | AAT | GAC | 1054 |
| His | Asn | Leu | Ile | Ser | Tyr | Met | Leu | Leu | Met | Lys | Val | Asn | Lys | Asn | Asp | |
| | | | | 340 | | | | | 345 | | | | | 350 | | |
| ATC | CGC | AAG | AAG | GTG | AGG | CGC | CTA | ATG | GGA | AAG | TCG | CAC | ATT | GGG | CTT | 1102 |
| Ile | Arg | Lys | Lys | Val | Arg | Arg | Leu | Met | Gly | Lys | Ser | His | Ile | Gly | Leu | |
| | | | 355 | | | | | 360 | | | | | 365 | | | |
| GTG | TAC | AGC | CAG | CAA | ATC | AAT | GAG | GTG | CTT | GAT | CAG | CTG | GCG | AAC | CTG | 1150 |
| Val | Tyr | Ser | Gln | Gln | Ile | Asn | Glu | Val | Leu | Asp | Gln | Leu | Ala | Asn | Leu | |
| | | 370 | | | | | 375 | | | | | 380 | | | | |

| | | | | | | | | | | | | | | | | |
|---|---|---|---|---|---|---|---|---|---|---|---|---|---|---|---|---|
| AAT | GGA | CGC | GAT | CTC | TCT | ATC | TGG | TCC | AGT | GGC | AGC | CGG | CAC | ATG | AAG | 1198 |
| Asn | Gly | Arg | Asp | Leu | Ser | Ile | Trp | Ser | Ser | Gly | Ser | Arg | His | Met | Lys | |
| | 385 | | | | 390 | | | | | 395 | | | | | | |
| AAG | CAG | ACA | TTT | GTG | GTA | CAT | GCA | GGG | ACA | GAT | ACA | AAC | GGA | GAT | ATC | 1246 |
| Lys | Gln | Thr | Phe | Val | Val | His | Ala | Gly | Thr | Asp | Thr | Asn | Gly | Asp | Ile | |
| 400 | | | | | 405 | | | | | 410 | | | | | 415 | |
| TTT | TTC | ATG | GAG | GTG | TGC | GAT | GAC | TGT | GTG | GTG | TTG | CGT | AGT | AAC | ATC | 1294 |
| Phe | Phe | Met | Glu | Val | Cys | Asp | Asp | Cys | Val | Val | Leu | Arg | Ser | Asn | Ile | |
| | | | | 420 | | | | | 425 | | | | | 430 | | |
| GGA | ACA | GTG | TAT | GAG | CGC | TGG | TGG | TAC | GAG | AAG | CTC | ATC | AAC | ATG | ACC | 1342 |
| Gly | Thr | Val | Tyr | Glu | Arg | Trp | Trp | Tyr | Glu | Lys | Leu | Ile | Asn | Met | Thr | |
| | | | 435 | | | | | 440 | | | | | 445 | | | |
| TAC | TGT | CCC | AAG | ACG | AAG | GTG | TTG | TGC | TTG | TGG | CGT | AGA | AAT | GGC | TCT | 1390 |
| Tyr | Cys | Pro | Lys | Thr | Lys | Val | Leu | Cys | Leu | Trp | Arg | Arg | Asn | Gly | Ser | |
| | | 450 | | | | | 455 | | | | | 460 | | | | |
| GAG | ACC | CAG | CTC | AAC | AAG | TTC | TAT | ACT | AAA | AAG | TGT | CGG | GAG | CTG | TAC | 1438 |
| Glu | Thr | Gln | Leu | Asn | Lys | Phe | Tyr | Thr | Lys | Lys | Cys | Arg | Glu | Leu | Tyr | |
| 465 | | | | | 470 | | | | | 475 | | | | | | |
| TAC | TGT | GTG | AAG | GAC | AGC | ATG | GAG | CGC | GCT | GCC | GCC | CGA | CAG | CAA | AGC | 1486 |
| Tyr | Cys | Val | Lys | Asp | Ser | Met | Glu | Arg | Ala | Ala | Ala | Arg | Gln | Gln | Ser | |
| 480 | | | | | 485 | | | | | 490 | | | | | 495 | |
| ATC | AAA | CCC | GGA | CCT | GAA | TTG | GGT | GGC | GAG | TTC | CCT | GTG | CAG | GAC | CTG | 1534 |
| Ile | Lys | Pro | Gly | Pro | Glu | Leu | Gly | Gly | Glu | Phe | Pro | Val | Gln | Asp | Leu | |
| | | | | 500 | | | | | 505 | | | | | 510 | | |
| AAG | ACT | GGT | GAG | GGT | GGC | CTG | CTG | CAG | GTG | ACC | CTG | GAA | GGG | ATC | AAC | 1582 |
| Lys | Thr | Gly | Glu | Gly | Gly | Leu | Leu | Gln | Val | Thr | Leu | Glu | Gly | Ile | Asn | |
| | | | | 515 | | | | | 520 | | | | | 525 | | |
| CTC | AAA | TTC | ATG | CAC | AAT | CAG | GTT | TTC | ATA | GAG | CTG | AAT | CAC | ATT | AAA | 1630 |
| Leu | Lys | Phe | Met | His | Asn | Gln | Val | Phe | Ile | Glu | Leu | Asn | His | Ile | Lys | |
| | | | 530 | | | | | 535 | | | | | 540 | | | |
| AAG | TGC | AAT | ACA | GTT | CGA | GGC | GTC | TTT | GTC | CTG | GAG | GAA | TTT | GTT | CCT | 1678 |
| Lys | Cys | Asn | Thr | Val | Arg | Gly | Val | Phe | Val | Leu | Glu | Glu | Phe | Val | Pro | |
| | 545 | | | | | 550 | | | | | 555 | | | | | |
| GAA | ATT | AAA | GAA | GTG | GTG | AGC | CAC | AAG | TAC | AAG | ACA | CCA | ATG | GCC | CAC | 1726 |
| Glu | Ile | Lys | Glu | Val | Val | Ser | His | Lys | Tyr | Lys | Thr | Pro | Met | Ala | His | |
| 560 | | | | | 565 | | | | | 570 | | | | | 575 | |
| GAA | ATC | TGC | TAC | TCC | GTA | TTA | TGT | CTC | TTC | TCG | TAC | GTG | GCT | GCA | GTT | 1774 |
| Glu | Ile | Cys | Tyr | Ser | Val | Leu | Cys | Leu | Phe | Ser | Tyr | Val | Ala | Ala | Val | |
| | | | | 580 | | | | | 585 | | | | | 590 | | |
| CAT | AGC | AGT | GAG | GAA | GAT | CTC | AGA | ACC | CCG | CCC | CGG | CCT | GTC | TCT | AGC | 1822 |
| His | Ser | Ser | Glu | Glu | Asp | Leu | Arg | Thr | Pro | Pro | Arg | Pro | Val | Ser | Ser | |
| | | | 595 | | | | | 600 | | | | | 605 | | | |

| | | | | | |
|---|---|---|---|---|---|
| TGATGGAGAG | GGGCTACGCA | GCTGCCCCAG | CCCAGGGCAC | GCCCCTGGCC | CCTTGCTGTT | 1882 |
| CCCAAGTGCA | CGATGCTGCT | GTGACTGAGG | AGTGGATGAT | GCTCGTGTGT | CCTCTGCAAG | 1942 |
| CCCCCTGCTG | TGGCTTGGTT | GGTTACCGGT | TATGTGTCCC | TCTGAGTGTG | TCTTGAGCGT | 2002 |
| GTCCACCTTC | TCCCTCTCCA | CTCCCAGAAG | ACCAAACTGC | CTTCCCCTCA | GGGCTCAAGA | 2062 |
| ATGTGTACAG | TCTGTGGGGC | CGGTGTGAAC | CCACTATTTT | GTGTCCTTGA | CATTTGTG | 2122 |
| TTGTGGTTCC | TTGTCCTTGT | CCCTGGCGTT | ATAACTGTCC | ACTGCAAGAG | TCTGGCTCTC | 2182 |
| CCTTCTCTGT | GACCCGGCAT | GACTGGGCGC | CTGGAGCAGT | TCACTCTGT | GAGGAGTGAG | 2242 |
| GGAACCCTGG | GGCTCACCCT | CTCAGAGGAA | GGGCACAGAG | AGGAAGGGAA | GAATTGGGGG | 2302 |
| GCAGCCGGAG | TGAGTGGCAG | CCTCCCTGCT | TCCTTCTGCA | TTCCCAAGCC | GGCAGCTACT | 2362 |
| GCCCAGGGCC | CGCAGTGTTG | GCTGCTGCCT | GCCACAGCCT | CTGTGACTGC | AGTGGAGCGG | 2422 |
| CGAATTCCCT | GTGGCCTGCC | ACGCCTTCGG | CATCAGAGGA | TGGAGTGGTC | GAGGCTAGTG | 2482 |
| GAGTCCCAGG | GACCGCTGGC | TGCTCTGCCT | GAGCATCAGG | GAGGGGGCAG | GAAAGACCAA | 2542 |

```
GCTGGGTTTG   CACATCTGTC   TGCAGGCTGT   CTCTCCAGGC   ACGGGGTGTC   AGGAGGGAGA        2602

GACAGCCTGG   GTATGGGCAA   GAAATGACTG   TAAATATTTC   AGCCCCACAT   TATTTATAGA        2662

AAATGTACAG   TTGTGTGAAT   GTGAAATAAA   TGTCCTCAAC   TCCCAAAAAA   AAAAAAAAA         2722

AAAAAAAAAA   AAA                                                                  2735
```

(2) INFORMATION FOR SEQ ID NO:12:

(i) SEQUENCE CHARACTERISTICS:
        (A) LENGTH: 607 amino acids
        (B) TYPE: amino acid
        (D) TOPOLOGY: linear (ii) MOLECULE TYPE: protein (xi) SEQUENCE DESCRIPTION: SEQ ID NO:12:

```
Glu  Ile  Ser  Arg  Lys  Val  Tyr  Lys  Gly  Met  Leu  Asp  Leu  Leu  Lys  Cys
  1              5                        10                       15

Thr  Val  Leu  Ser  Leu  Glu  Gln  Ser  Tyr  Ala  His  Ala  Gly  Leu  Gly  Gly
              20                       25                       30

Met  Ala  Ser  Ile  Phe  Gly  Leu  Leu  Glu  Ile  Ala  Gln  Thr  His  Tyr  Tyr
         35                       40                       45

Ser  Lys  Glu  Pro  Asp  Lys  Arg  Lys  Arg  Ser  Pro  Thr  Glu  Ser  Val  Asn
    50                       55                       60

Thr  Pro  Val  Gly  Lys  Asp  Pro  Gly  Leu  Ala  Gly  Arg  Gly  Asp  Pro  Lys
 65                       70                       75                       80

Ala  Met  Ala  Gln  Leu  Arg  Val  Pro  Gln  Leu  Gly  Pro  Arg  Ala  Pro  Ser
                   85                       90                       95

Ala  Thr  Gly  Lys  Gly  Pro  Lys  Glu  Leu  Asp  Thr  Arg  Ser  Leu  Lys  Glu
                  100                      105                      110

Glu  Asn  Phe  Ile  Ala  Ser  Ile  Gly  Pro  Glu  Val  Ile  Lys  Pro  Val  Phe
              115                      120                      125

Asp  Leu  Gly  Glu  Thr  Glu  Glu  Lys  Lys  Ser  Gln  Ile  Ser  Ala  Asp  Ser
         130                      135                      140

Gly  Val  Ser  Leu  Thr  Ser  Ser  Gln  Arg  Thr  Asp  Gln  Asp  Ser  Val
145                      150                      155                      160

Ile  Gly  Val  Ser  Pro  Ala  Val  Met  Ile  Arg  Ser  Ser  Ser  Gln  Asp  Ser
                  165                      170                      175

Glu  Val  Ser  Thr  Val  Val  Ser  Asn  Ser  Ser  Gly  Glu  Thr  Leu  Gly  Ala
              180                      185                      190

Asp  Ser  Asp  Leu  Ser  Ser  Asn  Ala  Gly  Asp  Gly  Pro  Gly  Gly  Glu  Gly
         195                      200                      205

Ser  Val  His  Leu  Ala  Ser  Ser  Arg  Gly  Thr  Leu  Ser  Asp  Ser  Glu  Ile
    210                      215                      220

Glu  Thr  Asn  Ser  Ala  Thr  Ser  Thr  Ile  Phe  Gly  Lys  Ala  His  Ser  Leu
225                      230                      235                      240

Lys  Pro  Ser  Ile  Lys  Glu  Lys  Leu  Ala  Gly  Ser  Pro  Ile  Arg  Thr  Ser
                  245                      250                      255

Glu  Asp  Val  Ser  Gln  Arg  Val  Tyr  Leu  Tyr  Glu  Gly  Leu  Leu  Gly  Lys
              260                      265                      270

Glu  Arg  Ser  Thr  Leu  Trp  Asp  Gln  Met  Gln  Phe  Trp  Glu  Asp  Ala  Phe
         275                      280                      285

Leu  Asp  Ala  Val  Met  Leu  Glu  Arg  Glu  Gly  Met  Gly  Met  Asp  Gln  Gly
    290                      295                      300

Pro  Gln  Glu  Met  Ile  Asp  Arg  Tyr  Leu  Ser  Leu  Gly  Glu  His  Asp  Arg
305                      310                      315                      320
```

| Lys | Arg | Leu | Glu | Asp | Asp | Glu | Asp | Arg | Leu | Leu | Ala | Thr | Leu | Leu | His |
|---|---|---|---|---|---|---|---|---|---|---|---|---|---|---|---|
| | | | | 325 | | | | 330 | | | | | | 335 | |

| Asn | Leu | Ile | Ser | Tyr | Met | Leu | Leu | Met | Lys | Val | Asn | Lys | Asn | Asp | Ile |
|---|---|---|---|---|---|---|---|---|---|---|---|---|---|---|---|
| | | | 340 | | | | | 345 | | | | 350 | | | |

| Arg | Lys | Lys | Val | Arg | Arg | Leu | Met | Gly | Lys | Ser | His | Ile | Gly | Leu | Val |
|---|---|---|---|---|---|---|---|---|---|---|---|---|---|---|---|
| | | 355 | | | | | 360 | | | | | 365 | | | |

| Tyr | Ser | Gln | Gln | Ile | Asn | Glu | Val | Leu | Asp | Gln | Leu | Ala | Asn | Leu | Asn |
|---|---|---|---|---|---|---|---|---|---|---|---|---|---|---|---|
| | 370 | | | | | 375 | | | | 380 | | | | | |

| Gly | Arg | Asp | Leu | Ser | Ile | Trp | Ser | Ser | Gly | Ser | Arg | His | Met | Lys | Lys |
|---|---|---|---|---|---|---|---|---|---|---|---|---|---|---|---|
| 385 | | | | | 390 | | | | | 395 | | | | | 400 |

| Gln | Thr | Phe | Val | Val | His | Ala | Gly | Thr | Asp | Thr | Asn | Gly | Asp | Ile | Phe |
|---|---|---|---|---|---|---|---|---|---|---|---|---|---|---|---|
| | | | | 405 | | | | | 410 | | | | | 415 | |

| Phe | Met | Glu | Val | Cys | Asp | Asp | Cys | Val | Val | Leu | Arg | Ser | Asn | Ile | Gly |
|---|---|---|---|---|---|---|---|---|---|---|---|---|---|---|---|
| | | | 420 | | | | | 425 | | | | | 430 | | |

| Thr | Val | Tyr | Glu | Arg | Trp | Trp | Tyr | Glu | Lys | Leu | Ile | Asn | Met | Thr | Tyr |
|---|---|---|---|---|---|---|---|---|---|---|---|---|---|---|---|
| | | 435 | | | | | 440 | | | | | 445 | | | |

| Cys | Pro | Lys | Thr | Lys | Val | Leu | Cys | Leu | Trp | Arg | Arg | Asn | Gly | Ser | Glu |
|---|---|---|---|---|---|---|---|---|---|---|---|---|---|---|---|
| | 450 | | | | | 455 | | | | | 460 | | | | |

| Thr | Gln | Leu | Asn | Lys | Phe | Tyr | Thr | Lys | Lys | Cys | Arg | Glu | Leu | Tyr | Tyr |
|---|---|---|---|---|---|---|---|---|---|---|---|---|---|---|---|
| 465 | | | | | 470 | | | | | 475 | | | | | 480 |

| Cys | Val | Lys | Asp | Ser | Met | Glu | Arg | Ala | Ala | Ala | Arg | Gln | Gln | Ser | Ile |
|---|---|---|---|---|---|---|---|---|---|---|---|---|---|---|---|
| | | | | 485 | | | | | 490 | | | | | 495 | |

| Lys | Pro | Gly | Pro | Glu | Leu | Gly | Gly | Glu | Phe | Pro | Val | Gln | Asp | Leu | Lys |
|---|---|---|---|---|---|---|---|---|---|---|---|---|---|---|---|
| | | | 500 | | | | | 505 | | | | | 510 | | |

| Thr | Gly | Glu | Gly | Gly | Leu | Leu | Gln | Val | Thr | Leu | Glu | Gly | Ile | Asn | Leu |
|---|---|---|---|---|---|---|---|---|---|---|---|---|---|---|---|
| | | 515 | | | | | 520 | | | | | 525 | | | |

| Lys | Phe | Met | His | Asn | Gln | Val | Phe | Ile | Glu | Leu | Asn | His | Ile | Lys | Lys |
|---|---|---|---|---|---|---|---|---|---|---|---|---|---|---|---|
| | 530 | | | | | 535 | | | | | 540 | | | | |

| Cys | Asn | Thr | Val | Arg | Gly | Val | Phe | Val | Leu | Glu | Glu | Phe | Val | Pro | Glu |
|---|---|---|---|---|---|---|---|---|---|---|---|---|---|---|---|
| 545 | | | | | 550 | | | | | 555 | | | | | 560 |

| Ile | Lys | Glu | Val | Val | Ser | His | Lys | Tyr | Lys | Thr | Pro | Met | Ala | His | Glu |
|---|---|---|---|---|---|---|---|---|---|---|---|---|---|---|---|
| | | | | 565 | | | | | 570 | | | | | 575 | |

| Ile | Cys | Tyr | Ser | Val | Leu | Cys | Leu | Phe | Ser | Tyr | Val | Ala | Ala | Val | His |
|---|---|---|---|---|---|---|---|---|---|---|---|---|---|---|---|
| | | | 580 | | | | | 585 | | | | | 590 | | |

| Ser | Ser | Glu | Glu | Asp | Leu | Arg | Thr | Pro | Pro | Arg | Pro | Val | Ser | Ser | |
|---|---|---|---|---|---|---|---|---|---|---|---|---|---|---|---|
| | | 595 | | | | | 600 | | | | | 605 | | | |

(2) INFORMATION FOR SEQ ID NO:13:

(i) SEQUENCE CHARACTERISTICS:
        (A) LENGTH: 3225 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 3..2846

(xi) SEQUENCE DESCRIPTION: SEQ ID NO:13:

| CC | CAG | ACT | CGC | CCC | GCC | CCA | GAG | ACT | GCG | CCT | GCG | CGG | GCA | CGA | GAC | 47 |
|---|---|---|---|---|---|---|---|---|---|---|---|---|---|---|---|---|
| | Gln | Thr | Arg | Pro | Ala | Pro | Glu | Thr | Ala | Pro | Ala | Arg | Ala | Arg | Asp | |
| | 1 | | | | 5 | | | | | 10 | | | | | 15 | |

| ACC | CTC | TCC | GCG | ATG | ACT | GCC | AGC | TCA | GTG | GAG | CAG | CTG | CGG | AAG | GAG | 95 |
|---|---|---|---|---|---|---|---|---|---|---|---|---|---|---|---|---|
| Thr | Leu | Ser | Ala | Met | Thr | Ala | Ser | Ser | Val | Glu | Gln | Leu | Arg | Lys | Glu | |
| | | | | 20 | | | | | 25 | | | | | 30 | | |

| | | | | | | | | | | | | | | | | |
|---|---|---|---|---|---|---|---|---|---|---|---|---|---|---|---|---|
| GGC | AAT | GAG | CTG | TTC | AAA | TGT | GGA | GAC | TAC | GGG | GGC | GCC | CTG | GCG | GCC | 143 |
| Gly | Asn | Glu | Leu | Phe | Lys | Cys | Gly | Asp | Tyr | Gly | Gly | Ala | Leu | Ala | Ala | |
| | | | 35 | | | | | 40 | | | | | 45 | | | |
| TAC | ACT | CAG | GCC | CTG | GGT | CTG | GAC | GCG | ACG | CCC | CAG | GAC | CAG | GCC | GTT | 191 |
| Tyr | Thr | Gln | Ala | Leu | Gly | Leu | Asp | Ala | Thr | Pro | Gln | Asp | Gln | Ala | Val | |
| | | | 50 | | | | | 55 | | | | | 60 | | | |
| CTG | CAC | CGG | AAC | CGG | GCC | GCC | TGC | CAC | CTC | AAG | CTG | GAA | GAT | TAC | GAC | 239 |
| Leu | His | Arg | Asn | Arg | Ala | Ala | Cys | His | Leu | Lys | Leu | Glu | Asp | Tyr | Asp | |
| | 65 | | | | | 70 | | | | | 75 | | | | | |
| AAA | GCA | GAA | ACA | GAG | GCA | TCC | AAA | GCC | ATT | GAA | AAG | GAT | GGT | GGG | GAT | 287 |
| Lys | Ala | Glu | Thr | Glu | Ala | Ser | Lys | Ala | Ile | Glu | Lys | Asp | Gly | Gly | Asp | |
| 80 | | | | | 85 | | | | | 90 | | | | | 95 | |
| GTC | AAA | GCA | CTC | TAC | CGG | CGG | AGC | CAA | GCC | CTA | GAG | AAG | CTG | GGC | CGC | 335 |
| Val | Lys | Ala | Leu | Tyr | Arg | Arg | Ser | Gln | Ala | Leu | Glu | Lys | Leu | Gly | Arg | |
| | | | | 100 | | | | | 105 | | | | | 110 | | |
| CTG | GAC | CAG | GCT | GTC | CTT | GAC | CTG | CAG | AGA | TGT | GTG | AGC | TTG | GAG | CCC | 383 |
| Leu | Asp | Gln | Ala | Val | Leu | Asp | Leu | Gln | Arg | Cys | Val | Ser | Leu | Glu | Pro | |
| | | | 115 | | | | | 120 | | | | | 125 | | | |
| AAG | AAC | AAA | GTT | TTC | CAG | GAG | GCC | TTG | CGG | AAC | ATC | GGG | GGC | CAG | ATT | 431 |
| Lys | Asn | Lys | Val | Phe | Gln | Glu | Ala | Leu | Arg | Asn | Ile | Gly | Gly | Gln | Ile | |
| | | 130 | | | | | 135 | | | | | 140 | | | | |
| CAG | GAG | AAG | GTG | CGA | TAC | ATG | TCC | TCG | ACG | GAT | GCC | AAA | GTG | GAA | CAG | 479 |
| Gln | Glu | Lys | Val | Arg | Tyr | Met | Ser | Ser | Thr | Asp | Ala | Lys | Val | Glu | Gln | |
| 145 | | | | | 150 | | | | | 155 | | | | | | |
| ATG | TTT | CAG | ATA | CTG | TTG | GAC | CCA | GAA | GAG | AAG | GGC | ACT | GAG | AAA | AAG | 527 |
| Met | Phe | Gln | Ile | Leu | Leu | Asp | Pro | Glu | Glu | Lys | Gly | Thr | Glu | Lys | Lys | |
| 160 | | | | | 165 | | | | | 170 | | | | | 175 | |
| CAA | AAG | GCT | TCT | CAG | AAC | CTG | GTG | GTG | CTG | GCC | AGG | GAG | GAT | GCT | GGA | 575 |
| Gln | Lys | Ala | Ser | Gln | Asn | Leu | Val | Val | Leu | Ala | Arg | Glu | Asp | Ala | Gly | |
| | | | | 180 | | | | | 185 | | | | | 190 | | |
| GCG | GAG | AAG | ATC | TTC | CGG | AGT | AAT | GGG | GTT | CAG | CTC | TTG | CAA | CGT | TTA | 623 |
| Ala | Glu | Lys | Ile | Phe | Arg | Ser | Asn | Gly | Val | Gln | Leu | Leu | Gln | Arg | Leu | |
| | | | 195 | | | | | 200 | | | | | 205 | | | |
| CTG | GAC | ATG | GGA | GAG | ACT | GAC | CTC | ATG | CTG | GCG | GCT | CTG | CGT | ACG | CTG | 671 |
| Leu | Asp | Met | Gly | Glu | Thr | Asp | Leu | Met | Leu | Ala | Ala | Leu | Arg | Thr | Leu | |
| | | 210 | | | | | 215 | | | | | 220 | | | | |
| GTT | GGC | ATT | TGC | TCT | GAG | CAT | CAG | TCA | CGG | ACA | GTG | GCA | ACC | CTG | AGC | 719 |
| Val | Gly | Ile | Cys | Ser | Glu | His | Gln | Ser | Arg | Thr | Val | Ala | Thr | Leu | Ser | |
| 225 | | | | | 230 | | | | | 235 | | | | | | |
| ATA | CTG | GGA | ACT | CGG | CGA | GTA | GTC | TCC | ATC | CTG | GGC | GTG | GAA | AGC | CAG | 767 |
| Ile | Leu | Gly | Thr | Arg | Arg | Val | Val | Ser | Ile | Leu | Gly | Val | Glu | Ser | Gln | |
| 240 | | | | | 245 | | | | | 250 | | | | | 255 | |
| GCT | GTG | TCC | CTG | GCT | GCC | TGC | CAC | CTG | CTG | CAG | GTT | ATG | TTT | GAT | GCC | 815 |
| Ala | Val | Ser | Leu | Ala | Ala | Cys | His | Leu | Leu | Gln | Val | Met | Phe | Asp | Ala | |
| | | | | 260 | | | | | 265 | | | | | 270 | | |
| CTC | AAG | GAA | GGT | GTC | AAA | AAA | GGC | TTC | CGA | GGC | AAA | GAA | GGT | GCC | ATC | 863 |
| Leu | Lys | Glu | Gly | Val | Lys | Lys | Gly | Phe | Arg | Gly | Lys | Glu | Gly | Ala | Ile | |
| | | | | 275 | | | | | 280 | | | | | 285 | | |
| ATT | GTG | GAT | CCT | GCC | CGG | GAG | CTG | AAG | GTC | CTC | ATC | AGT | AAC | CTC | TTA | 911 |
| Ile | Val | Asp | Pro | Ala | Arg | Glu | Leu | Lys | Val | Leu | Ile | Ser | Asn | Leu | Leu | |
| | | 290 | | | | | 295 | | | | | 300 | | | | |
| GAT | CTG | CTG | ACA | GAG | GTG | GGG | GTC | TCT | GGC | CAA | GGC | CGA | GAC | AAT | GCC | 959 |
| Asp | Leu | Leu | Thr | Glu | Val | Gly | Val | Ser | Gly | Gln | Gly | Arg | Asp | Asn | Ala | |
| | | 305 | | | | | 310 | | | | | 315 | | | | |
| CTG | ACC | CTC | CTG | ATT | AAA | GCG | GTG | CCC | CGG | AAG | TCT | CTC | AAG | GAC | CCC | 1007 |
| Leu | Thr | Leu | Leu | Ile | Lys | Ala | Val | Pro | Arg | Lys | Ser | Leu | Lys | Asp | Pro | |
| 320 | | | | | 325 | | | | | 330 | | | | | 335 | |
| AAC | AAC | AGC | CTC | ACC | CTC | TGG | GTC | ATC | GAC | CAA | GGT | CTG | AAA | AAG | ATT | 1055 |
| Asn | Asn | Ser | Leu | Thr | Leu | Trp | Val | Ile | Asp | Gln | Gly | Leu | Lys | Lys | Ile | |
| | | | | 340 | | | | | 345 | | | | | 350 | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TTG | GAA | GTG | GGG | GGC | TCT | CTA | CAG | GAC | CCT | CCT | GGG | GAG | CTC | GCA | GTG | 1103 |
| Leu | Glu | Val | Gly | Gly | Ser | Leu | Gln | Asp | Pro | Pro | Gly | Glu | Leu | Ala | Val |      |
|     |     |     | 355 |     |     |     | 360 |     |     |     |     | 365 |     |     |     |      |
| ACC | GCA | AAC | AGC | CGC | ATG | AGC | GCC | TCT | ATT | CTC | CTC | AGC | AAG | CTC | TTT | 1151 |
| Thr | Ala | Asn | Ser | Arg | Met | Ser | Ala | Ser | Ile | Leu | Leu | Ser | Lys | Leu | Phe |      |
|     |     | 370 |     |     |     | 375 |     |     |     |     | 380 |     |     |     |     |      |
| GAT | GAC | CTC | AAG | TGT | GAT | GCG | GAG | AGG | GAG | AAT | TTC | CAC | AGA | CTT | TGT | 1199 |
| Asp | Asp | Leu | Lys | Cys | Asp | Ala | Glu | Arg | Glu | Asn | Phe | His | Arg | Leu | Cys |      |
| 385 |     |     |     |     | 390 |     |     |     |     | 395 |     |     |     |     |     |      |
| GAA | AAC | TAC | ATC | AAG | AGC | TGG | TTT | GAG | GGC | CAA | GGG | CTG | GCC | GGG | AAG | 1247 |
| Glu | Asn | Tyr | Ile | Lys | Ser | Trp | Phe | Glu | Gly | Gln | Gly | Leu | Ala | Gly | Lys |      |
| 400 |     |     |     |     | 405 |     |     |     |     | 410 |     |     |     |     | 415 |      |
| CTA | CGG | GCC | ATC | CAG | ACG | GTG | TCC | TGC | CTC | CTG | CAG | GGC | CCA | TGT | GAC | 1295 |
| Leu | Arg | Ala | Ile | Gln | Thr | Val | Ser | Cys | Leu | Leu | Gln | Gly | Pro | Cys | Asp |      |
|     |     |     |     | 420 |     |     |     |     | 425 |     |     |     |     | 430 |     |      |
| GCT | GGC | AAC | CGG | GCC | TTG | GAG | CTG | AGC | GGT | GTC | ATG | GAG | AGT | GTG | ATT | 1343 |
| Ala | Gly | Asn | Arg | Ala | Leu | Glu | Leu | Ser | Gly | Val | Met | Glu | Ser | Val | Ile |      |
|     |     |     | 435 |     |     |     |     | 440 |     |     |     |     | 445 |     |     |      |
| GCT | CTG | TGT | GCC | TCT | GAG | CAG | GAG | GAG | GAG | CAG | CTG | GTG | GCC | GTG | GAG | 1391 |
| Ala | Leu | Cys | Ala | Ser | Glu | Gln | Glu | Glu | Glu | Gln | Leu | Val | Ala | Val | Glu |      |
|     |     | 450 |     |     |     |     | 455 |     |     |     |     | 460 |     |     |     |      |
| GCT | CTG | ATC | CAT | GCA | GCC | GGC | AAG | GCT | AAG | CGG | GCC | TCA | TTC | ATC | ACT | 1439 |
| Ala | Leu | Ile | His | Ala | Ala | Gly | Lys | Ala | Lys | Arg | Ala | Ser | Phe | Ile | Thr |      |
| 465 |     |     |     |     | 470 |     |     |     |     | 475 |     |     |     |     |     |      |
| GCC | AAT | GGT | GTC | TCG | CTG | CTG | AAG | GAC | CTA | TAT | AAG | TGC | AGC | GAG | AAG | 1487 |
| Ala | Asn | Gly | Val | Ser | Leu | Leu | Lys | Asp | Leu | Tyr | Lys | Cys | Ser | Glu | Lys |      |
| 480 |     |     |     |     | 485 |     |     |     |     | 490 |     |     |     |     | 495 |      |
| GAC | AGC | ATC | CGC | ATC | CGG | GCG | CTA | GTG | GGA | CTC | TGT | AAG | CTC | GGT | TCG | 1535 |
| Asp | Ser | Ile | Arg | Ile | Arg | Ala | Leu | Val | Gly | Leu | Cys | Lys | Leu | Gly | Ser |      |
|     |     |     |     | 500 |     |     |     |     | 505 |     |     |     |     | 510 |     |      |
| GCT | GGA | GGG | ACT | GAC | TTC | AGC | ATG | AAG | CAG | TTT | GCT | GAA | GGC | TCC | ACT | 1583 |
| Ala | Gly | Gly | Thr | Asp | Phe | Ser | Met | Lys | Gln | Phe | Ala | Glu | Gly | Ser | Thr |      |
|     |     |     | 515 |     |     |     |     | 520 |     |     |     |     | 525 |     |     |      |
| CTC | AAA | CTG | GCT | AAG | CAG | TGT | CGA | AAG | TGG | CTG | TGC | AAT | GAC | CAG | ATC | 1631 |
| Leu | Lys | Leu | Ala | Lys | Gln | Cys | Arg | Lys | Trp | Leu | Cys | Asn | Asp | Gln | Ile |      |
|     |     | 530 |     |     |     |     | 535 |     |     |     |     | 540 |     |     |     |      |
| GAC | GCA | GGC | ACT | CGG | CGC | TGG | GCA | GTG | GAG | GGC | CTG | GCT | TAC | CTG | ACC | 1679 |
| Asp | Ala | Gly | Thr | Arg | Arg | Trp | Ala | Val | Glu | Gly | Leu | Ala | Tyr | Leu | Thr |      |
|     |     | 545 |     |     |     |     | 550 |     |     |     |     | 555 |     |     |     |      |
| TTT | GAT | GCC | GAC | GTG | AAG | GAA | GAG | TTT | GTG | GAG | GAT | GCG | GCT | GCT | CTG | 1727 |
| Phe | Asp | Ala | Asp | Val | Lys | Glu | Glu | Phe | Val | Glu | Asp | Ala | Ala | Ala | Leu |      |
| 560 |     |     |     |     | 565 |     |     |     |     | 570 |     |     |     |     | 575 |      |
| AAA | GCT | CTG | TTC | CAG | CTC | AGC | AGG | TTG | GAG | GAG | AGG | TCA | GTG | CTC | TTT | 1775 |
| Lys | Ala | Leu | Phe | Gln | Leu | Ser | Arg | Leu | Glu | Glu | Arg | Ser | Val | Leu | Phe |      |
|     |     |     |     | 580 |     |     |     |     | 585 |     |     |     |     | 590 |     |      |
| GCG | GTG | GCC | TCA | GCG | CTG | GTG | AAC | TGC | ACC | AAC | AGC | TAT | GAC | TAC | GAG | 1823 |
| Ala | Val | Ala | Ser | Ala | Leu | Val | Asn | Cys | Thr | Asn | Ser | Tyr | Asp | Tyr | Glu |      |
|     |     |     | 595 |     |     |     |     | 600 |     |     |     |     | 605 |     |     |      |
| GAG | CCC | GAC | CCC | AAG | ATG | GTG | GAG | CTG | GCC | AAG | TAT | GCC | AAG | CAG | CAT | 1871 |
| Glu | Pro | Asp | Pro | Lys | Met | Val | Glu | Leu | Ala | Lys | Tyr | Ala | Lys | Gln | His |      |
|     |     | 610 |     |     |     |     | 615 |     |     |     |     | 620 |     |     |     |      |
| GTG | CCC | GAG | CAG | CAC | CCC | AAG | GAC | AAG | CCA | AGC | TTC | GTG | CGG | GCT | CGG | 1919 |
| Val | Pro | Glu | Gln | His | Pro | Lys | Asp | Lys | Pro | Ser | Phe | Val | Arg | Ala | Arg |      |
|     |     | 625 |     |     |     |     | 630 |     |     |     |     | 635 |     |     |     |      |
| GTG | AAG | AAG | CTG | CTG | GCA | GCG | GGT | GTG | GTG | TCG | GCC | ATG | GTG | TGC | ATG | 1967 |
| Val | Lys | Lys | Leu | Leu | Ala | Ala | Gly | Val | Val | Ser | Ala | Met | Val | Cys | Met |      |
| 640 |     |     |     |     | 645 |     |     |     |     | 650 |     |     |     |     | 655 |      |
| GTG | AAG | ACG | GAG | AGC | CCT | GTG | CTG | ACC | AGT | TCC | TGC | AGA | GAG | CTG | CTC | 2015 |
| Val | Lys | Thr | Glu | Ser | Pro | Val | Leu | Thr | Ser | Ser | Cys | Arg | Glu | Leu | Leu |      |
|     |     |     |     | 660 |     |     |     |     | 665 |     |     |     |     | 670 |     |      |

| | | | | | | | | | | | | | | | | |
|---|---|---|---|---|---|---|---|---|---|---|---|---|---|---|---|---|
|TCC|AGG|GTC|TTC|TTG|GCT|TTA|GTG|GAA|GAG|GTA|GAG|GAC|CGA|GGC|ACT|2063|
|Ser|Arg|Val 675|Phe|Leu|Ala|Leu|Val 680|Glu|Glu|Val|Glu|Asp|Arg 685|Gly|Thr| |
|GTG|GTT|GCC|CAG|GGA|GGC|GGC|AGG|GCG|CTG|ATC|CCG|CTG|GCC|CTG|GAA|2111|
|Val|Val|Ala 690|Gln|Gly|Gly|Gly|Arg 695|Ala|Leu|Ile|Pro|Leu 700|Ala|Leu|Glu| |
|GGC|ACG|GAC|GTG|GGG|CAG|ACA|AAG|GCA|GCC|CAG|GCC|CTT|GCC|AAG|CTC|2159|
|Gly|Thr|Asp 705|Val|Gly|Gln|Thr|Lys 710|Ala|Ala|Gln|Ala|Leu 715|Ala|Lys|Leu| |
|ACC|ATC|ACC|TCC|AAC|CCG|GAG|ATG|ACC|TTC|CCT|GGC|GAG|CGG|ATC|TAT|2207|
|Thr|Ile|Thr 720|Ser|Asn|Pro|Glu|Met 725|Thr|Phe|Pro|Gly|Glu 730|Arg|Ile|Tyr 735|
|GAG|GTG|GTC|CGG|CCC|CTC|GTC|TCC|CTG|TTG|CAC|CTC|AAC|TGC|TCA|GGC|2255|
|Glu|Val|Val|Arg 740|Pro|Leu|Val|Ser|Leu 745|Leu|His|Leu|Asn|Cys 750|Ser|Gly|
|CTG|CAG|AAC|TTC|GAG|GCG|CTC|ATG|GCC|CTA|ACA|AAC|CTG|GCT|GGG|ATC|2303|
|Leu|Gln|Asn|Phe 755|Glu|Ala|Leu|Met|Ala 760|Leu|Thr|Asn|Leu|Ala 765|Gly|Ile|
|AGC|GAG|AGG|CTC|CGG|CAG|AAG|ATC|CTG|AAG|GAG|AAG|GCT|GTG|CCC|ATG|2351|
|Ser|Glu|Arg 770|Leu|Arg|Gln|Lys|Ile 775|Leu|Lys|Glu|Lys|Ala 780|Val|Pro|Met|
|ATA|GAA|GGC|TAC|ATG|TTT|GAG|GAG|CAT|GAG|ATG|ATC|CGC|CGG|GCA|GCC|2399|
|Ile|Glu|Gly 785|Tyr|Met|Phe|Glu|Glu 790|His|Glu|Met|Ile|Arg 795|Arg|Ala|Ala|
|ACG|GAG|TGC|ATG|TGT|AAC|TTG|GCC|ATG|AGC|AAG|GAG|GTG|CAG|GAC|CTC|2447|
|Thr|Glu|Cys 800|Met|Cys|Asn|Leu|Ala 805|Met|Ser|Lys|Glu|Val 810|Gln|Asp|Leu 815|
|TTC|GAA|GCC|CAG|GGC|AAT|GAC|CGA|CTG|AAG|CTG|CTG|GTG|CTG|TAC|AGT|2495|
|Phe|Glu|Ala|Gln 820|Gly|Asn|Asp|Arg|Leu 825|Lys|Leu|Leu|Val|Leu 830|Tyr|Ser|
|GGA|GAG|GAT|GAT|GAG|CTG|CTA|CAG|CGG|GCA|GCT|GCC|GGG|GGC|TTG|GCC|2543|
|Gly|Glu|Asp|Asp 835|Glu|Leu|Leu|Gln|Arg 840|Ala|Ala|Ala|Gly|Gly 845|Leu|Ala|
|ATG|CTT|ACC|TCC|ATG|CGG|CCC|ACG|CTC|TGC|AGC|CGC|ATT|CCC|CAA|GTG|2591|
|Met|Leu|Thr 850|Ser|Met|Arg|Pro|Thr 855|Leu|Cys|Ser|Arg|Ile 860|Pro|Gln|Val|
|ACC|ACA|CAC|TGG|CTG|GAG|ATC|CTG|CAG|GCC|CTG|CTT|CTG|AGC|TCC|AAC|2639|
|Thr|Thr|His 865|Trp|Leu|Glu|Ile|Leu 870|Gln|Ala|Leu|Leu|Leu 875|Ser|Ser|Asn|
|CAG|GAG|CTG|CAG|CAC|CGG|GGT|GCT|GTG|GTG|GTG|CTG|AAC|ATG|GTG|GAG|2687|
|Gln|Glu|Leu|Gln 880|His|Arg 885|Gly|Ala|Val|Val|Val 890|Leu|Asn|Met|Val|Glu 895|
|GCC|TCG|AGG|GAG|ATT|GCC|AGC|ACC|CTG|ATG|GAG|AGT|GAG|ATG|ATG|GAG|2735|
|Ala|Ser|Arg|Glu|Ile 900|Ala|Ser|Thr|Leu|Met 905|Glu|Ser|Glu|Met|Met 910|Glu|
|ATC|TTG|TCA|GTG|CTA|GCT|AAG|GGT|GAC|CAC|AGC|CCT|GTC|ACA|AGG|GCT|2783|
|Ile|Leu|Ser|Val 915|Leu|Ala|Lys|Gly|Asp 920|His|Ser|Pro|Val|Thr 925|Arg|Ala|
|GCT|GCA|GCC|TGC|CTG|GAC|AAA|GCA|GTG|GAA|TAT|GGG|CTT|ATC|CAA|CCC|2831|
|Ala|Ala|Ala 930|Cys|Leu|Asp|Lys|Ala 935|Val|Glu|Tyr|Gly|Leu 940|Ile|Gln|Pro|
|AAC|CAA|GAT|GGA|GAG|TGAGGGGTT|GTCCCTGGGC|CCAAGGCTCA|TGCACACGCT|2886|
|Asn|Gln|Asp|Gly|Glu| | | | | |
| | |945| | | | | | | |

| | | |
|---|---|---|
|ACCTATTGTG GCACGGAGAG TAAGGACGGA AGCAGCTTTG GCTGGTGGTG GCTGGCATGC|2946|
|CCAATACTCT TGCCCATCCT CGCTTGCTGC CCTAGGATGT CCTCTGTTCT GAGTCAGCGG|3006|
|CCACGTTCAG TCACACAGCC CTGCTTGGCC AGCACTGCCT GCAGCCTCAC TCAGAGGGGC|3066|
|CCTTTTTCTG TACTACTGTA GTCAGCTGGG AATGGGGAAG GTGCATCCCA ACACAGCCTG|3126|

TGGATCCTGG GGCATTTGGA AGGGCGCACA CATCAGCAGC CTCACCAGCT GTGAGCCTGC    3186

TATCAGGCCT GCCCCTCCAA TAAAAGTGTG TAGAACTCC    3225

( 2 ) INFORMATION FOR SEQ ID NO:14:

( i ) SEQUENCE CHARACTERISTICS:
( A ) LENGTH: 948 amino acids
( B ) TYPE: amino acid
( D ) TOPOLOGY: linear ( i i ) MOLECULE TYPE: protein ( x i ) SEQUENCE DESCRIPTION: SEQ ID NO:14:

```
Gln Thr Arg Pro Ala Pro Glu Thr Ala Pro Ala Arg Ala Arg Asp Thr
  1               5                  10                  15

Leu Ser Ala Met Thr Ala Ser Ser Val Gln Leu Arg Lys Glu Gly
             20                  25                  30

Asn Glu Leu Phe Lys Cys Gly Asp Tyr Gly Gly Ala Leu Ala Ala Tyr
             35                  40                  45

Thr Gln Ala Leu Gly Leu Asp Ala Thr Pro Gln Asp Gln Ala Val Leu
         50                  55                  60

His Arg Asn Arg Ala Ala Cys His Leu Lys Leu Glu Asp Tyr Asp Lys
 65                  70                  75                  80

Ala Glu Thr Glu Ala Ser Lys Ala Ile Glu Lys Asp Gly Gly Asp Val
                 85                  90                  95

Lys Ala Leu Tyr Arg Arg Ser Gln Ala Leu Glu Lys Leu Gly Arg Leu
                100                 105                 110

Asp Gln Ala Val Leu Asp Leu Gln Arg Cys Val Ser Leu Glu Pro Lys
             115                 120                 125

Asn Lys Val Phe Gln Glu Ala Leu Arg Asn Ile Gly Gly Gln Ile Gln
    130                 135                 140

Glu Lys Val Arg Tyr Met Ser Ser Thr Asp Ala Lys Val Glu Gln Met
145                 150                 155                 160

Phe Gln Ile Leu Leu Asp Pro Glu Glu Lys Gly Thr Glu Lys Lys Gln
                165                 170                 175

Lys Ala Ser Gln Asn Leu Val Val Leu Ala Arg Glu Asp Ala Gly Ala
                180                 185                 190

Glu Lys Ile Phe Arg Ser Asn Gly Val Gln Leu Leu Gln Arg Leu Leu
            195                 200                 205

Asp Met Gly Glu Thr Asp Leu Met Leu Ala Ala Leu Arg Thr Leu Val
    210                 215                 220

Gly Ile Cys Ser Glu His Gln Ser Arg Thr Val Ala Thr Leu Ser Ile
225                 230                 235                 240

Leu Gly Thr Arg Arg Val Val Ser Ile Leu Gly Val Glu Ser Gln Ala
                245                 250                 255

Val Ser Leu Ala Ala Cys His Leu Leu Gln Val Met Phe Asp Ala Leu
                260                 265                 270

Lys Glu Gly Val Lys Lys Gly Phe Arg Gly Lys Glu Gly Ala Ile Ile
            275                 280                 285

Val Asp Pro Ala Arg Glu Leu Lys Val Leu Ile Ser Asn Leu Leu Asp
    290                 295                 300

Leu Leu Thr Glu Val Gly Val Ser Gly Gln Gly Arg Asp Asn Ala Leu
305                 310                 315                 320

Thr Leu Leu Ile Lys Ala Val Pro Arg Lys Ser Leu Lys Asp Pro Asn
                325                 330                 335
```

-continued

```
Asn  Ser  Leu  Thr  Leu  Trp  Val  Ile  Asp  Gln  Gly  Leu  Lys  Lys  Ile  Leu
               340                 345                           350

Glu  Val  Gly  Gly  Ser  Leu  Gln  Asp  Pro  Pro  Gly  Glu  Leu  Ala  Val  Thr
          355                      360                      365

Ala  Asn  Ser  Arg  Met  Ser  Ala  Ser  Ile  Leu  Leu  Ser  Lys  Leu  Phe  Asp
370                      375                      380

Asp  Leu  Lys  Cys  Asp  Ala  Glu  Arg  Glu  Asn  Phe  His  Arg  Leu  Cys  Glu
385                 390                      395                           400

Asn  Tyr  Ile  Lys  Ser  Trp  Phe  Glu  Gly  Gln  Gly  Leu  Ala  Gly  Lys  Leu
                    405                      410                      415

Arg  Ala  Ile  Gln  Thr  Val  Ser  Cys  Leu  Gln  Gly  Pro  Cys  Asp  Ala
               420                      425                      430

Gly  Asn  Arg  Ala  Leu  Glu  Leu  Ser  Gly  Val  Met  Glu  Ser  Val  Ile  Ala
          435                      440                      445

Leu  Cys  Ala  Ser  Glu  Gln  Glu  Glu  Gln  Leu  Val  Ala  Val  Glu  Ala
     450                      455                      460

Leu  Ile  His  Ala  Ala  Gly  Lys  Ala  Lys  Arg  Ala  Ser  Phe  Ile  Thr  Ala
465                      470                      475                      480

Asn  Gly  Val  Ser  Leu  Leu  Lys  Asp  Leu  Tyr  Lys  Cys  Ser  Glu  Lys  Asp
                    485                      490                      495

Ser  Ile  Arg  Ile  Arg  Ala  Leu  Val  Gly  Leu  Cys  Lys  Leu  Gly  Ser  Ala
               500                      505                      510

Gly  Gly  Thr  Asp  Phe  Ser  Met  Lys  Gln  Phe  Ala  Glu  Gly  Ser  Thr  Leu
          515                      520                      525

Lys  Leu  Ala  Lys  Gln  Cys  Arg  Lys  Trp  Leu  Cys  Asn  Asp  Gln  Ile  Asp
     530                      535                      540

Ala  Gly  Thr  Arg  Arg  Trp  Ala  Val  Glu  Gly  Leu  Ala  Tyr  Leu  Thr  Phe
545                      550                      555                      560

Asp  Ala  Asp  Val  Lys  Glu  Glu  Phe  Val  Glu  Asp  Ala  Ala  Ala  Leu  Lys
                    565                      570                      575

Ala  Leu  Phe  Gln  Leu  Ser  Arg  Leu  Glu  Glu  Arg  Ser  Val  Leu  Phe  Ala
               580                      585                      590

Val  Ala  Ser  Ala  Leu  Val  Asn  Cys  Thr  Asn  Ser  Tyr  Asp  Tyr  Glu  Glu
          595                      600                      605

Pro  Asp  Pro  Lys  Met  Val  Glu  Leu  Ala  Lys  Tyr  Ala  Lys  Gln  His  Val
     610                      615                      620

Pro  Glu  Gln  His  Pro  Lys  Asp  Lys  Pro  Ser  Phe  Val  Arg  Ala  Arg  Val
625                      630                      635                      640

Lys  Lys  Leu  Leu  Ala  Ala  Gly  Val  Val  Ser  Ala  Met  Val  Cys  Met  Val
                    645                      650                      655

Lys  Thr  Glu  Ser  Pro  Val  Leu  Thr  Ser  Ser  Cys  Arg  Glu  Leu  Leu  Ser
               660                      665                      670

Arg  Val  Phe  Leu  Ala  Leu  Val  Glu  Glu  Val  Glu  Asp  Arg  Gly  Thr  Val
          675                      680                      685

Val  Ala  Gln  Gly  Gly  Gly  Arg  Ala  Leu  Ile  Pro  Leu  Ala  Leu  Glu  Gly
     690                      695                      700

Thr  Asp  Val  Gly  Gln  Thr  Lys  Ala  Ala  Gln  Ala  Leu  Ala  Lys  Leu  Thr
705                      710                      715                      720

Ile  Thr  Ser  Asn  Pro  Glu  Met  Thr  Phe  Pro  Gly  Glu  Arg  Ile  Tyr  Glu
                    725                      730                      735

Val  Val  Arg  Pro  Leu  Val  Ser  Leu  Leu  His  Leu  Asn  Cys  Ser  Gly  Leu
               740                      745                      750

Gln  Asn  Phe  Glu  Ala  Leu  Met  Ala  Leu  Thr  Asn  Leu  Ala  Gly  Ile  Ser
          755                      760                      765
```

```
Glu  Arg  Leu  Arg  Gln  Lys  Ile  Leu  Lys  Glu  Lys  Ala  Val  Pro  Met  Ile
     770                     775                      780

Glu  Gly  Tyr  Met  Phe  Glu  Glu  His  Glu  Met  Ile  Arg  Arg  Ala  Ala  Thr
785                      790                      795                          800

Glu  Cys  Met  Cys  Asn  Leu  Ala  Met  Ser  Lys  Glu  Val  Gln  Asp  Leu  Phe
                    805                      810                          815

Glu  Ala  Gln  Gly  Asn  Asp  Arg  Leu  Lys  Leu  Leu  Val  Leu  Tyr  Ser  Gly
                    820                      825                     830

Glu  Asp  Asp  Glu  Leu  Leu  Gln  Arg  Ala  Ala  Ala  Gly  Gly  Leu  Ala  Met
          835                      840                     845

Leu  Thr  Ser  Met  Arg  Pro  Thr  Leu  Cys  Ser  Arg  Ile  Pro  Gln  Val  Thr
     850                      855                      860

Thr  His  Trp  Leu  Glu  Ile  Leu  Gln  Ala  Leu  Leu  Leu  Ser  Ser  Asn  Gln
865                      870                      875                          880

Glu  Leu  Gln  His  Arg  Gly  Ala  Val  Val  Val  Leu  Asn  Met  Val  Glu  Ala
                    885                      890                          895

Ser  Arg  Glu  Ile  Ala  Ser  Thr  Leu  Met  Glu  Ser  Glu  Met  Met  Glu  Ile
               900                      905                     910

Leu  Ser  Val  Leu  Ala  Lys  Gly  Asp  His  Ser  Pro  Val  Thr  Arg  Ala  Ala
          915                      920                     925

Ala  Ala  Cys  Leu  Asp  Lys  Ala  Val  Glu  Tyr  Gly  Leu  Ile  Gln  Pro  Asn
     930                      935                      940

Gln  Asp  Gly  Glu
945
```

( 2 ) INFORMATION FOR SEQ ID NO:15:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:15:

```
Asp  Tyr  Lys  Asp  Asp  Asp  Asp  Lys
 1                    5
```

TNF RECEPTOR DEATH LIGAND PROTEINS AND INHIBITORS OF LIGAND BINDING

This application is a continuation-in-part of application Ser. No. 08/494,440, filed Jun. 19, 1995, which was a continuation-in-part of application Ser. No. 08/327,514, filed Oct. 19, 1994, now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor).

Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia et al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nucleotide 2 to nucleotide 931;

(j) a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD ligand protein comprising the amino acid sequence of SEQ ID NO:12;

(p) a polynucleotide encoding an TNF-R1-DD ligand protein comprising a fragment of the amino acid sequence of SEQ ID NO:12;

(q) a polynucleotide comprising the nucleotide sequence of SEQ ID NO:13 from nucleotide 3 to nucleotide 2846;

(r) a polynucleotide comprising a fragment of the nucleotide sequence of SEQ ID NO:13, which encodes a protein having TNF-R1-DD ligand protein activity;

(s) a polynucleotide encoding an TNF-R1-DD ligand protein comprising the amino acid sequence of SEQ ID NO:14;

(t) a polynucleotide encoding an TNF-R1-DD ligand protein comprising a fragment of the amino acid sequence of SEQ ID NO:14 and having TNF-R1-DD ligand protein activity; and (u) a polynucleotide capable of hybridizing under stringent conditions to any one of the polynucleotides specified in (a)–(t).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein, which comprises:

(a) growing a culture of the host cell transformed with such polynucleotide compositions in a suitable culture medium; and (b) purifying the TNF-R1-DD ligand protein from the culture.

The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:10;

(h) fragments of the amino acid sequence of SEQ ID NO:10;

(i) the amino acid sequence of SEQ ID NO:12;

(j) fragments of the amino acid sequence of SEQ ID NO:12;

(k) the amino acid sequence of SEQ ID NO:14; and (l) fragments of the amino acid sequence of SEQ ID NO:14;

the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture;

(b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:8;

(h) fragments of the amino acid sequence of SEQ ID NO:8;

(i) the amino acid sequence of SEQ ID NO:10;

(j) fragments of the amino acid sequence of SEQ ID NO:10;

(k) the amino acid sequence of SEQ ID NO:12;

(l) fragments of the amino acid sequence of SEQ ID NO:12;

(m) the amino acid sequence of SEQ ID NO:14; and (n) fragments of the amino acid sequence of SEQ ID NO:14.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1, which encodes a protein having TNF-R1-DD ligand protein activity;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2 and having TNF-R1-DD ligand protein activity;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3, which encodes a protein having TNF-R1-DD ligand protein activity;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4 and having TNF-R1-DD ligand protein activity;

(i) a polynucleotide comprising the nucleotide sequence of SEQ ID NO:5 from nucleotide 2 to nucleotide 559;

(j) a polynucleotide comprising a fragment of the nucleotide sequence of SEQ ID NO:5, which encodes a protein having TNF-R1-DD ligand protein activity;

(k) a polynucleotide encoding an TNF-R1-DD ligand protein comprising the amino acid sequence of SEQ ID NO:6;

(l) a polynucleotide encoding an TNF-R1-DD ligand protein comprising a fragment of the amino acid sequence of SEQ ID NO:6 and having TNF-R1-DD ligand protein activity;

(m) a polynucleotide comprising the nucleotide sequence of SEQ ID NO:7 from nucleotide 57 to nucleotide 875;

(n) a polynucleotide comprising a fragment of the nucleotide sequence of SEQ ID NO:7, which encodes a protein having TNF-R1-DD ligand protein activity;

(o) a polynucleotide encoding an TNF-R1-DD ligand protein comprising the amino acid sequence of SEQ ID NO:8;

(p) a polynucleotide encoding an TNF-R1-DD ligand protein comprising a fragment of the amino acid sequence of SEQ ID NO:8 and having TNF-R1-DD ligand protein activity;

(q) a polynucleotide comprising the nucleotide sequence of SEQ ID NO:9 from nucleotide 2 to nucleotide 931;

(r) a polynucleotide comprising a fragment of the nucleotide sequence of SEQ ID NO:9;

(s) a polynucleotide encoding an TNF-R1-DD ligand protein comprising the amino acid sequence of SEQ ID NO:10;

(t) a polynucleotide encoding an TNF-R1-DD ligand protein comprising a fragment of the amino acid sequence of SEQ ID NO:10;

(u) a polynucleotide comprising the nucleotide sequence of SEQ ID NO:11 from nucleotide 2 to nucleotide 1822;

(v) a polynucleotide comprising a fragment of the nucleotide sequence of SEQ ID NO:11;

(w) a polynucleotide encoding an TNF-R1-DD ligand protein comprising the amino acid sequence of SEQ ID NO:12;

(x) a polynucleotide encoding an TNF-R1-DD ligand protein comprising a fragment of the amino acid sequence of SEQ ID NO:12;

(y) a polynucleotide comprising the nucleotide sequence of SEQ ID NO:13 from nucleotide 3 to nucleotide 2846;

(z) a polynucleotide comprising a fragment of the nucleotide sequence of SEQ ID NO:13, which encodes a protein having TNF-R1-DD ligand protein activity;

(aa) a polynucleotide encoding an TNF-R1-DD ligand protein comprising the amino acid sequence of SEQ ID NO:14;

(bb) a polynucleotide encoding an TNF-R1-DD ligand protein comprising a fragment of the amino acid sequence of SEQ ID NO:14 and having TNF-R1-DD ligand protein activity; and (cc) a polynucleotide capable of hybridizing under stringent conditions to any one of the polynucleotides specified in (a)–(bb), which encodes a protein having TNF-R1-DD ligand protein activity.

BRIEF DESCRIPTION OF THE FIGURES

FIGS. 1 and 2 depict autoradiographs demonstrating the expression of TNF-R1-DD ligand proteins of the present invention.

FIG. 4 demonstrates the binding of 1TU and 27TU to TNF-R1-DD. MBP, MBP-1TU or MBP-27TU (3 µg) was incubated with glutathione beads containing 3 µg of either GST or GST-TNF-R1-DD in 100 µl of binding buffer (0.2% Triton, 20 mM Tris pH 7.5, 140 mM NaCl, 0.1 mM EDTA, 10 mM DTT and 5% glycerol). The reaction ws performed at 4° C. for 2 hours and centrifuged to remove unbound fraction (Unbound). The beads were then washed with 500 µl binding buffer four times and resuspended into SDS-sample buffer (Bound). These samples were analyzed by Western blot using anti-MBP antibody (New England Biolab).

DETAILED DESCRIPTION OF THE INVENTION

Figure 1:
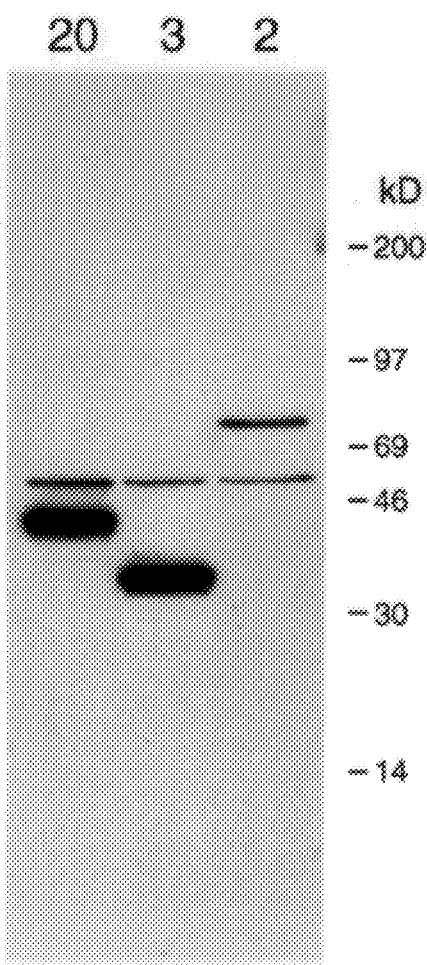

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD". The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

A full-length clone corresponding to clone 3DD was also isolated and identified as "clone 3TW". The nucleotide sequence of clone 3TW is reported as SEQ ID NO:13. Nucleotides 3 to 2846 of SEQ ID NO:13 encode a TNF-R1-DD ligand protein, the amino acid sequence of which is reported as SEQ ID NO:14. Amino acids 811 to 948 of SEQ ID NO:14 correspond to amino acids 1 to 138 of SEQ ID NO:4 (clone 3DD). Clone 3TW was deposited with the American Type Culture Collection on Sep. 26, 1995 and given the accession number ATCC 69904.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

The sequence of a polynucleotide encoding another such protein is set forth in SEQ ID NO:9 from nucleotides 2 to 931. This polynucleotide has been identified as "clone 1TU" The amino acid sequence of the TNF-R1-DD ligand protein encoded by clone 1TU is set forth in SEQ ID NO:10. It is believed that clone 1TU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASTX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU" The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

The protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO:12). Clone 15TU was deposited with the American Type Culture Collection on Jun. 7, 1995 and given the accession number ATCC 69847. 15TU comprises the same nucleotide sequence as 27TU over this region of amino acids.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-DD ligand protein is expressed by a host cell which has been transformed (transfected) with the ligated polynucleotide/expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag", SEQ ID NO:13) is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_0$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_0$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J.Amer.Chem.Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R1-DD ligand proteins generally.

EXAMPLE 1

Cloning of TNF-R Death Domain Ligand Protein Encoding Polynucleotide

A yeast genetic selection method, the "interaction trap" [Gyuris et al, Cell 75:791–803, 1993, which is incorporated herein by reference], was used to screen W138 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18–34 ($Ura^+$), which carries another reporter sequence, LexAop-lacZ. For screening cDNAs encoding proteins that interact with TNF-R1-DD, the expression vector pJG4–5 (TRP1), containing the W138 cell cDNA library (see below for the cDNA library construction), was transformed into the above strain (EGY48/pEG202-TNF-R1-DD/pSH18–34) according to the method described by Gietz et al., Nucleic Acids Res., 20:1425 (1992).

cDNA Library Construction:

W138 cell cDNA library: Double stranded cDNA was prepared from 3 ug of W138 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4–5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1\times10^6$ colonies were plated on LB plates containing 100 ug/ml of ampicillin. These *E.coli* were scraped, pooled, and a large scale plasmid prep was performed using the Wizard Maxi Prep kit (Promega, Madison, Wis.), yielding 3.2 mg of supercoiled plasmid DNA.

W138 Cell cDNA Screening Results:

$1\times10^6$ transformants were obtained on glucose $Ura^-His^-Trp^-$ plates. These transformants were pooled and resuspended in a solution of 65% glycerol, 10 mM Tris-HCl (pH 7.5), 10 mM $MgCl_2$ and stored at −80° C. in 1 mL aliquots. For screening purposes, aliquots of these were diluted 10-fold into $Ura^-His^-Trp^-$ CM dropout gal/raff medium (containing 2% galactose, 1% raffinose), which induces the expresssion of the library encoded proteins, and incubated at 30° C. for 4 hours. $12\times10^6$ colony forming units (CFUs) were then plated on standard 10 cm galactose X-Gal $Ura^-His^-Trp^-Leu^-$ plates at a density of $2\times10^5$ CFU/plate. After three days at 30° C., about 1,000 colonies were formed ($Leu^+$) and of those, sixty-four colonies were $LacZ^+$. In order to test if the $Leu^+/LacZ^+$ phenotype was due to the library-encoded protein, the galactose dependency of the phenotype was tested. Expression of the library-encoded proteins was turned off by growth on glucose $Ura^-His^-Trp^-$ master plates and then retested for galactose-dependency on glucose $Ura^-His^-Trp^-Leu^-$, galactose $Ura^-His^-Trp^-Leu^-$, glucose X-Gal $Ura^-His^-Trp^-$, and galactose X-Gal $Ura^-His^-Trp^-$ plates. Of these, 32 colonies showed galactose-dependent growth on $Leu^-$ plates and galactose-dependent blue color on X-Gal-containing medium ($LacZ^+$ phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4–5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4–5 containing these clones sequences were rescued from yeast by transforming the total yeast DNAs into the *E. coli* strain KC8 and selecting for growth on Trp-ampicillin plates. These putative TNFR1 interacting proteins were then tested further for specificity of interaction with the TNF-R1-DD by the reintroduction of JG4–5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results:

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones, 15TU and 27TU, encode related or identical sequences, except that 27TU contains about 864 additional nucleotides (or about 288 amino acids) at the 5' end. 15/27TU also encode a novel sequence.

EXAMPLE 2

Expression of the TNF-R1-DD Ligand Protein cDNAs encoding TNF-R intracellular ligand proteins were released from the pJG4–5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlue-BacHis (Invitrogen) for baculovirus/insect expression. For the immunodetection of TNF-R intracellular ligand expression in mammalian cells, an epitope sequence, "Flag," (SEQ ID NO:13) was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys (SEQ ID NO:13). Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide (SEQ ID NO:13), can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

FIGS. 1 and 2 depict autoradiographs demonstrating the expression of TNF-R1-DD ligand proteins in yeast and mammalian cells. FIG. 1 shows the results of expression of isloated clones of the present invention in yeast. EGY48 was transformed with pJG4–5 containing clone 2DD, 3DD or 20DD. Cells were then grown overnight in the galactose/raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty μg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

Assays of TNF-R Death Domain Binding

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GST-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

Characterization of TNF-R Death Domain Ligand Protein

Mapping the interaction site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-mediated response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or functional assays

The signal transduction events initiated by TNF binding to its receptor are still largely unknown. However, one major result of TNF binding is the stimulation of cellular serine/threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

Isolation of Full Length Clones

In many cases, cDNAs obtained from the interaction trap method each encode only a portion of the fill length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

Antibodies Specific for TNF-R Intracellular Ligand Protein

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

Characterization of Clones 1TU and 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $P^{75}{}_{IC}$), the entire intracellular domain of TNF-R (TNF-R $P^{55}{}_{IC}$), the death domain of the fas antigen (which shares 28% identity with TNF-R-DD) ($Fas_{DD}$), the Drosophila transcription factor bicoid, and a region of the IL-1 receptor known to be critical for signalling ($IL-1R_{477-527}$). As shown in Table 1, none of these clones interacted with TNF-R $P^{75}{}_{IC}$ or $Fas_{DD}$, and only 1TU interacted with bicoid. In contrast, both 1TU and 15TU bound the cytoplasmic domain of the p55 TNF-R, as well as residues 477–527 of the IL-1R. 27TU interacted relatively weakly with these sequences.

TABLE 1

| clone | TNF-$R_{DD}$ | TNF-R $p75_{IC}$ | TNF-R $p55_{IC}$ | $Fas_{DD}$ | bicoid | IL-1R (477–527) |
|---|---|---|---|---|---|---|
| 1TU | +++ | − | +++ | − | ++ | +++ |
| 15TU | +++ | ± | +++ | − | − | ++ |
| 27TU | +++ | − | + | − | − | + |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | TNF-$R_{DD}$ | F345A | L351A | W378A | I408A |
|---|---|---|---|---|---|
| 1TU | +++ | + | ++ | ++ | + |
| 15TU | +++ | + | + | ++ | ++ |
| 27TU | +++ | + | + | ± | ++ |

Expression of 1TU, 15TU and 27TU

Figure 3A:
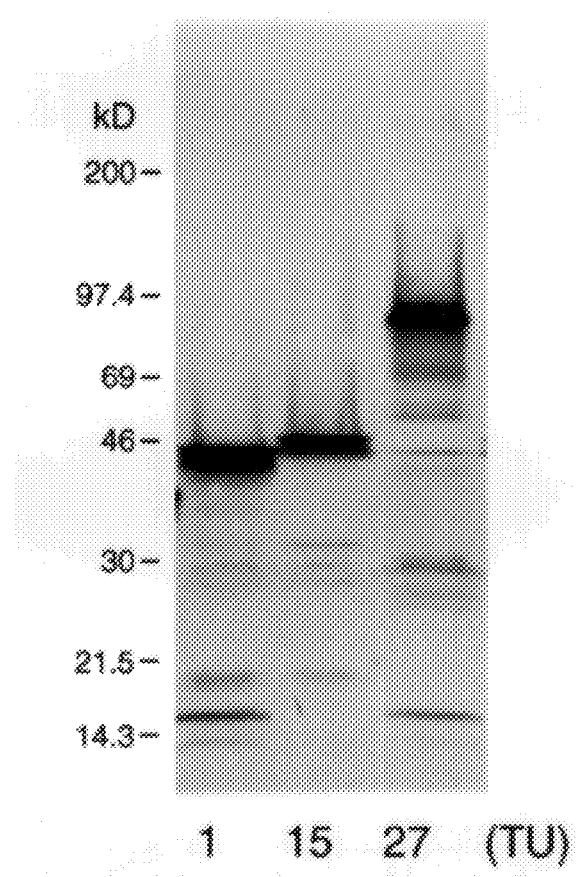
FIGS. 3A and 3B depict autoradiographs demonstrating the expression of clones 1TU, 15TU and 27TU.
Figure 3B:
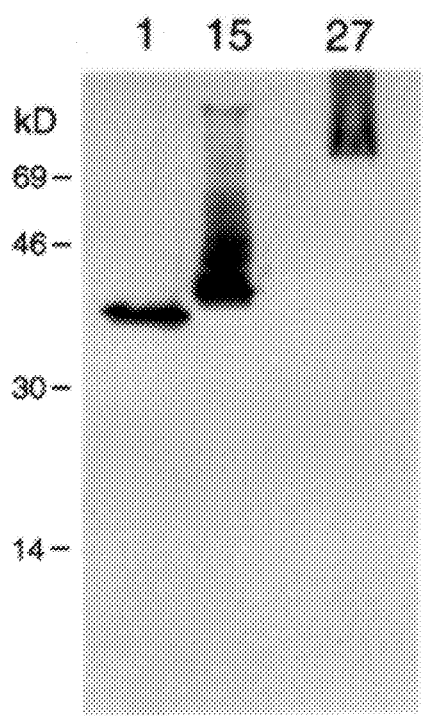

FIG. 3 depicts an autoradiograph demonstrating the expression of clones 1TU, 15TU and 27TU in yeast (A) and COS cells (B).

In (A): EGY48 was transformed with pJG4–5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

The interaction of 1TU and 27TU with TNF-R1-DD was tested using purified bacterially expressed fusion proteins. As shown in FIG. 4, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation of JNK Activity

Figure 5:
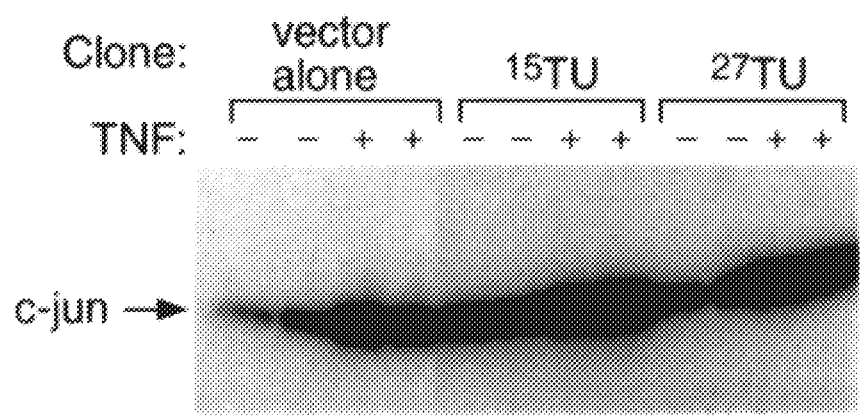
FIG. 5 demonstrates the ability of 15TU and 27TU to activate the JNK pathway. COS cells were contransfected with HA-tagged JNK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

EXAMPLE 8

Isolation, Expression and Assay of Clone 3TW

Clone 3TW was isolated from the WI38 cDNA library using clone 3DD as a porbe. Clone 3TW was expressed.

Figure 6:
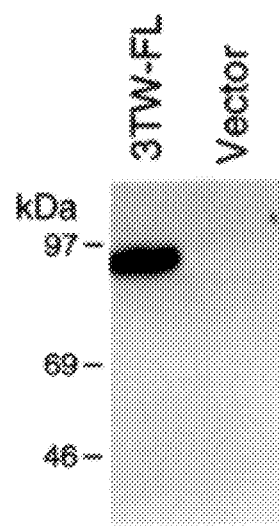
FIG. 6 is an autoradiograph of an SDS-PAGE gel of conditioned media from COS cells transfected with clone 3TW.

FIG. 6 is an autoradiograph which demonstrates expression of 3TW (indicated by arrow).

Figure 7:
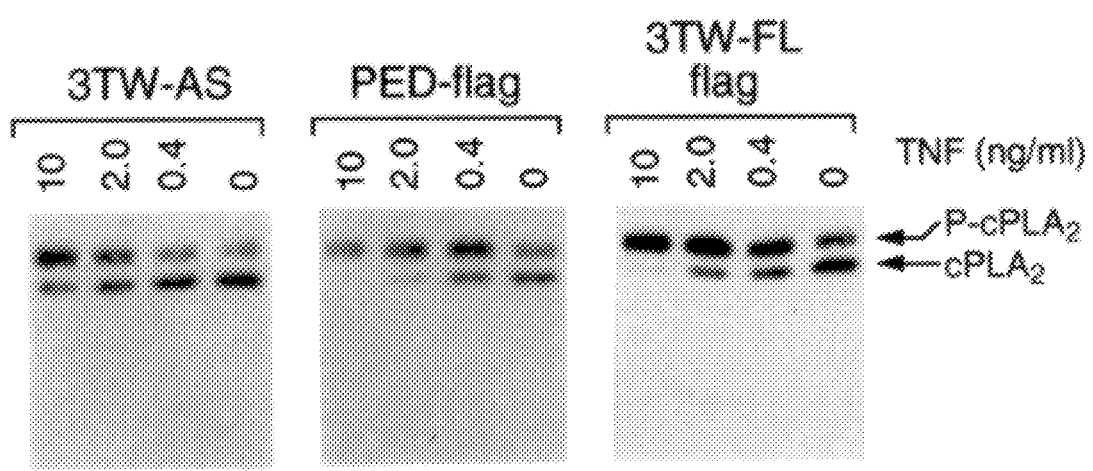
FIG. 7 is an autoradiograph which demonstrates that an antisense oligonucleotide derived from the sequence of clone 3TW inhibits TNF-induced cPLA$_2$ phosphorylation.

An antisense oligonucleotide was derived from the sequence of clone 3TW. The antisense oligonucleotide was assayed to determine its ability to inhibit TNF-induced cPLA$_2$ phosphorylation. FIG. 7 depicts the results of that experiment. Activity of the anitsense oligonucleotide (3TWAS) was compared with the full-length clone (3TWFL), Flag-3TW full length (3TWFLflag) and pED-flag vector (pEDflag). The antisense oligonucleotide inhibited phosphorylation.

---

What is claimed is:

1. A composition comprising a protein having TNF-R1-DD ligand protein activity wherein said protein comprises an amino acid sequence selected from the group consisting of:
   (a) the amino acid sequence of SEQ ID NO:4; and
   (b) fragments of the amino acid sequence of SEQ ID NO:4;
said protein being substantially free from other mammalian proteins.

2. The composition of claim 1 wherein said protein comprises the amino acid sequence of SEQ ID NO:4.

3. The composition of claim 1, further comprising a pharmaceutically acceptable carrier.

4. A composition comprising a protein having TNF-R1-DD ligand protein activity wherein said protein comprises an amino acid sequence selected from the group consisting of:
   (a) the amino acid sequence of SEQ ID NO:14; and
   (b) fragments of the amino acid sequence of SEQ ID NO:14;
said protein being substantially free from other mammalian proteins.

5. The composition of claim 4 wherein said protein comprises the amino acid sequence of SEQ ID NO:14.

6. The composition of claim 4, further comprising a pharmaceutically acceptable carrier.

7. TNF-R1-DD ligand protein produced according to a method comprising:
   (a) transforming a host cell with a composition comprising an isolated polynucleotide operably linked to an expression control sequence and encoding a TNF-R1-DD ligand protein comprising the amino acid sequence of SEQ ID NO:14;
   (b) growing a culture of the host cell in a suitable culture medium; and
   (c) purifying the TNF-R1-DD ligand protein from the culture.

* * * * *